US007815803B2

(12) United States Patent
Kobold et al.

(10) Patent No.: US 7,815,803 B2
(45) Date of Patent: Oct. 19, 2010

(54) PREPARATION OF SAMPLES FOR LC-MS/MS USING MAGNETIC PARTICLES

(75) Inventors: Uwe Kobold, Weilheim (DE); Albert Geiger, Penzberg (DE); Rupert Herrmann, Weilheim (DE); Michael Vogeser, Munich (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 317 days.

(21) Appl. No.: 12/133,545

(22) Filed: Jun. 5, 2008

(65) Prior Publication Data

US 2009/0090855 A1  Apr. 9, 2009

(30) Foreign Application Priority Data

Jun. 14, 2007  (EP) .................................. 07011633
Mar. 14, 2008  (EP) .................................. 08004796

(51) Int. Cl.
*B01D 15/08* (2006.01)
*B01D 59/44* (2006.01)
*H01J 49/00* (2006.01)

(52) U.S. Cl. .................... 210/635; 210/198.2; 250/282; 536/25.41; 73/1.02

(58) Field of Classification Search ................ 250/282; 210/635, 198.2; 536/25.41; 73/1.02
See application file for complete search history.

(56) References Cited

U.S. PATENT DOCUMENTS 3,843,540 A   10/1974  Reimers et al.

3,966,410 A  * 6/1976  Jahnsen ....................... 436/178
2009/0139908 A1 * 6/2009  Zhou et al. ................... 209/225

FOREIGN PATENT DOCUMENTS

| WO | 0026927 A1 | 5/2000 |
| WO | 2005015216 A1 | 2/2005 |
| WO | 2006075185 A1 | 7/2006 |

OTHER PUBLICATIONS

Anonymous, Dynabeads RPC 18, Invitrogen Manual (online), 2007.
Alnouti, Y. et al., "Development and application of a new on-line SPE system combined with LC-MS/MS detection for high throughput direct analysis of pharmaceutical compounds in plasma," Journal of Chromatography A, 1080 (2005) 99-106.

(Continued)

*Primary Examiner*—Nikita Wells
(74) *Attorney, Agent, or Firm*—Marilyn L. Amick; Roche Diagnostics Operations, Inc.

(57) ABSTRACT

The present invention provides a novel procedure of preparing samples for analysis by way of mass spectrometry, preferably LC-MS/MS. Accordingly, functionalized magnetic particles with a hydrophobic surface were used for extracting low molecular weight compounds from complex liquid biological samples such as plasma, serum, whole blood or hemolyzed blood. The method of the invention includes (a) contacting the sample with an amount of functionalized magnetic particles with a hydrophobic surface, (b) incubating the sample and the particles, thereby adsorbing the compound to the hydrophobic surface, (c) separating the particles by applying a magnetic field and removing the liquid, (d) optionally washing the particles, (e) eluting the compound from the particles.

11 Claims, 15 Drawing Sheets

A

B

OTHER PUBLICATIONS

Annesley, T., "Ion Suppression in Mass Spectrometry," Clinical Chemistry, 49:7 (2003) 1041-1044.

Breivold, E., et al, "Sample Preparation for Plasma and Serum Profiling Using Magnetic Bead Technology," Invitrogen Poster (online), 2005.

Fazili, Z, et al., "Erythrocyte Folate Extraction and Quantitative Determination by Liquid Chromatography—Tandem Mass Spectrometry: Comparison of Results with Microbiologic Assay," Clinical Chemistry 51:12 (2005) 2318-2325.

Gunter, E., et al., "Results of an international round robin for serum and whole-blood folate," Clinical Chemistry, (1996) 1696-1694.

Jones, K., et al., "An Immunoassay for the Measurement of Sirolimus," Clinical Therapeutics, vol. 22, Suppl B (2000) B49-B61.

Koal, T. et al., "Direct and fast determination of antietroviral drugs by automated online solid-phase extraction-liquid chromatography-tandem mass spectrometry in human plasma," Clin Chem Lab Med 44:3 (2006) 299-305.

Murthy, J. et al., "Tacrolimus Metabolite Cross-Reactivity in Different Tacrolimus Assays," Clinical Biochemistry, vol. 31 (Nov. 31, 1998) 613-617.

Namvar, L. et al., "Detection and Typing of Herpes Simplex Virus (HSV) in Mucocutaneous Samples by TaqMan PCR Targeting a gB Segment Homologous for HSV Types 1 and 2," Journal of Clinical Microbiology 43:5 (May 2005) 2058-2064.

Pfeiffer, C. et al., "Determination of FOlate Vitamers in Human Serum by Stable-Isotope-Dilution Tandem Mass Spectrometry and Comparison with Radioassay and Microbilogic Assay,"Clinical Chemistry 50:2 (2004) 423-432.

Porstmann, T. et al., Journal of Immunological Methods, 150 (1992) 5-21.

Tarning, J. et al., "Development and validation of an automated solid phase extraction and liquid chromatographic method for the determination of piperaquine in urine," Journal of Pharmaceutical and Biomedical Analysis 41 @006) 213-218.

Villanueva, J. et al., "Serum Peptide Profiling y Magnetic Particle-Assisted, Automated Sample Processing and MALDI-TOF Mass spectrometry," Anal. Chem. 76 (2004) 1560-1570.

Villanueva, J. et al., "Automated serum peptide profiling," Nature Protocols 1:2 (2006) 880-891.

Vogesser, M., "Liquid Chromatography-Tandem Mass Spectrometry—Application in the Clinical Laboratory," Clinic Chem Lab med 41:2 (2003) 117-126.

Vogeser, M. et al., "Determination of Itraconazole and Hydroxyitraconazole in Plasma by Use of Liquid Chromatography-Tandem Mass Spectrometry with on-line Solid-Phase Extraction," Clin Chem Lab Med 41:7 (2003) 915-920.

Vogeser, M. et al., "Automated processing of whole blood samples for the determination of immunosuppressants by liquid chromatography tandem-mass spectrometry," Clin Chem Lab Med 44:9 (2006) 1126-1130.

Williams, M. et al., "Rapid determination of rat plasma uridine levels by HPLC-ESi-MS utilizing the Captiva™ filter plates for sample preparation," Biomedical Chromatography 17 (2003) 215-218.

Yang, L. et al., "Validation and application of an automated 96-well solid-phase extraction liquid chromatography-tandem mass spectrometry method for the quantitative determination of SCH 201781 in human plasma," Journal of Chromatography B, 809 (2004) 75-80.

Zhang, X. et al., "Evaluation of a Novel, Integrated Approach Using Functionalized Magnetic Beads, Bench-Top MALDI-TOF-MS with Prestructured Sample Supports, and Pattern Recognition Software for Profiling Potential Biomarkers in Human Plasma," Journal of Biomolecular Techniques 15 (2004) 167-175.

"Therapeutic drug monitoring—is it important for newer immunosuppressive agents?" Drugs Ther Perspect 17;22 (2001) 8pp.

Ramirez, L. et al., "Magnetic Polystyrene Nanoparticles with a High Magnetite Content Obtained by Miniemulsion Porcesses," Macromol Chem Phys 204 (2003) 22-31.

* cited by examiner

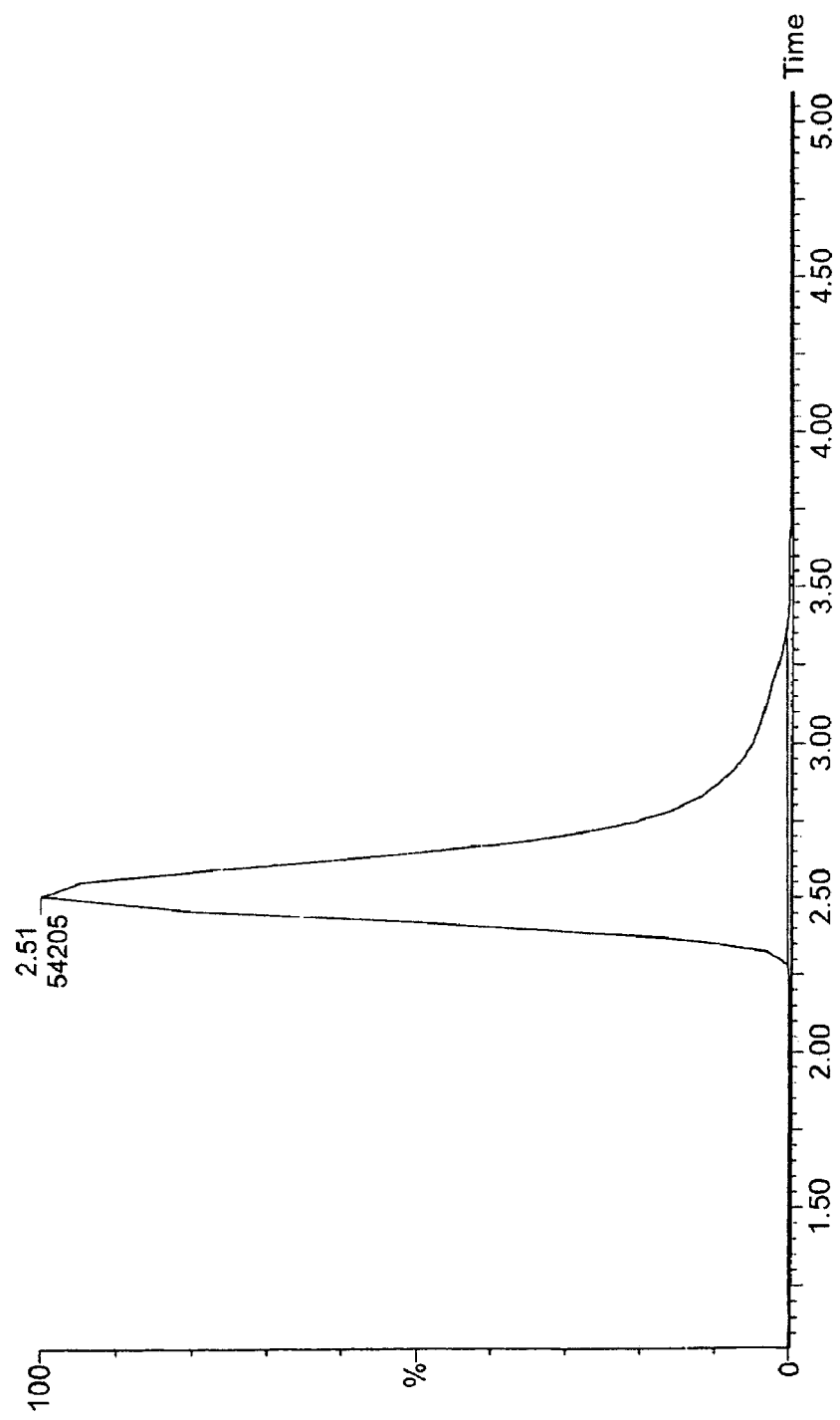

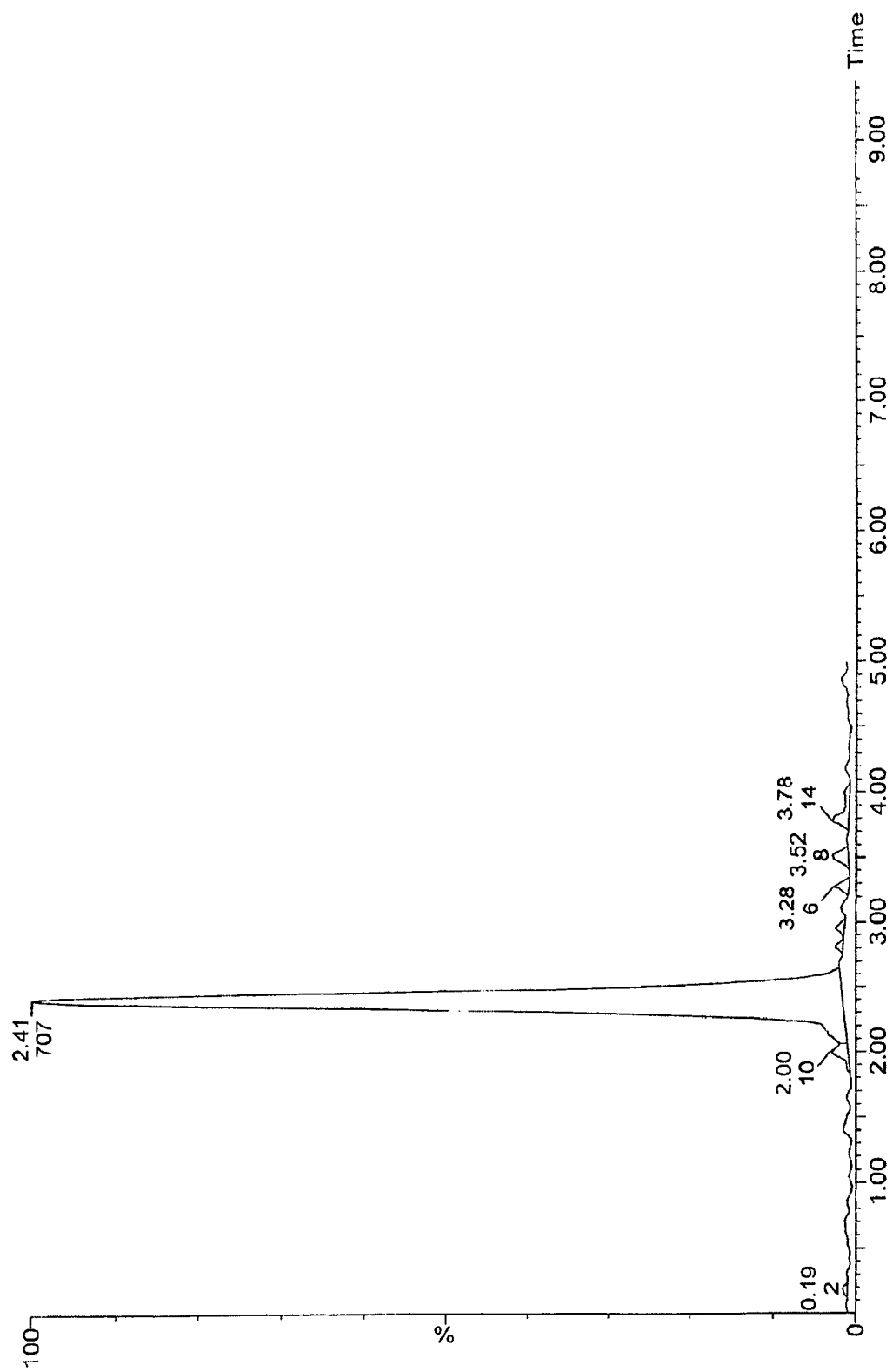
Fig. 3(a)(1)

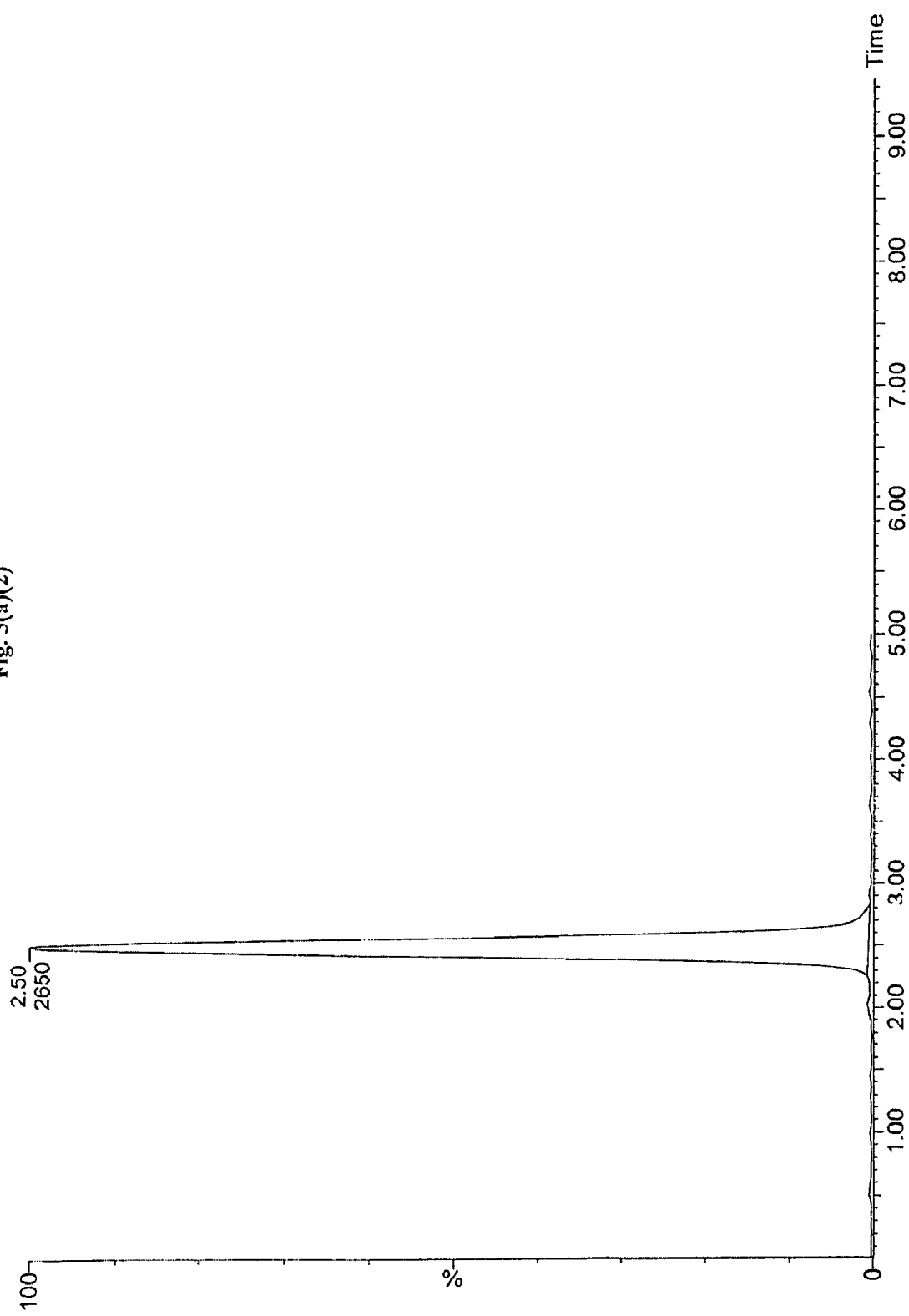
Fig. 3(a)(2)

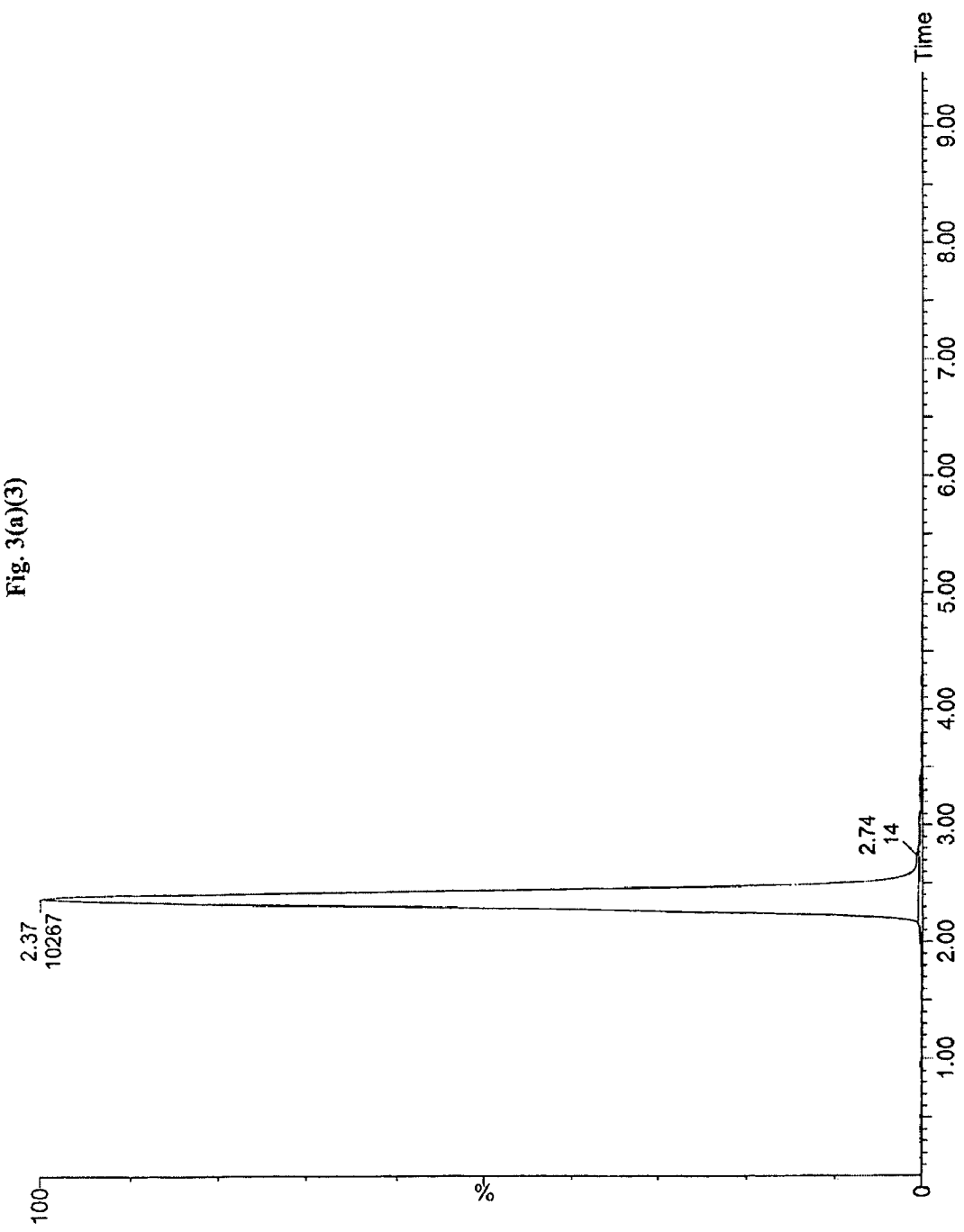
Fig. 3(a)(3)

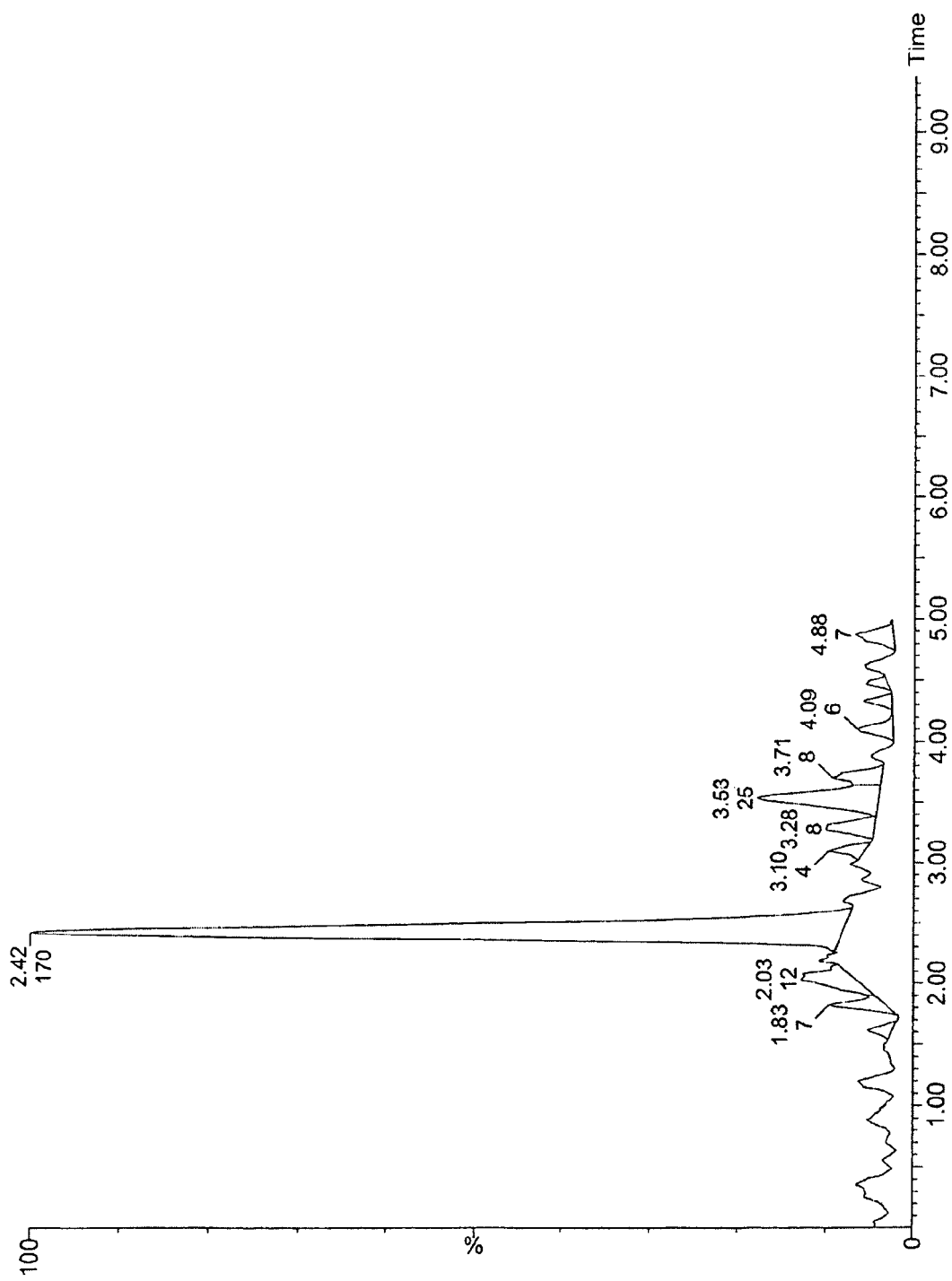
Fig. 3(b)(1)

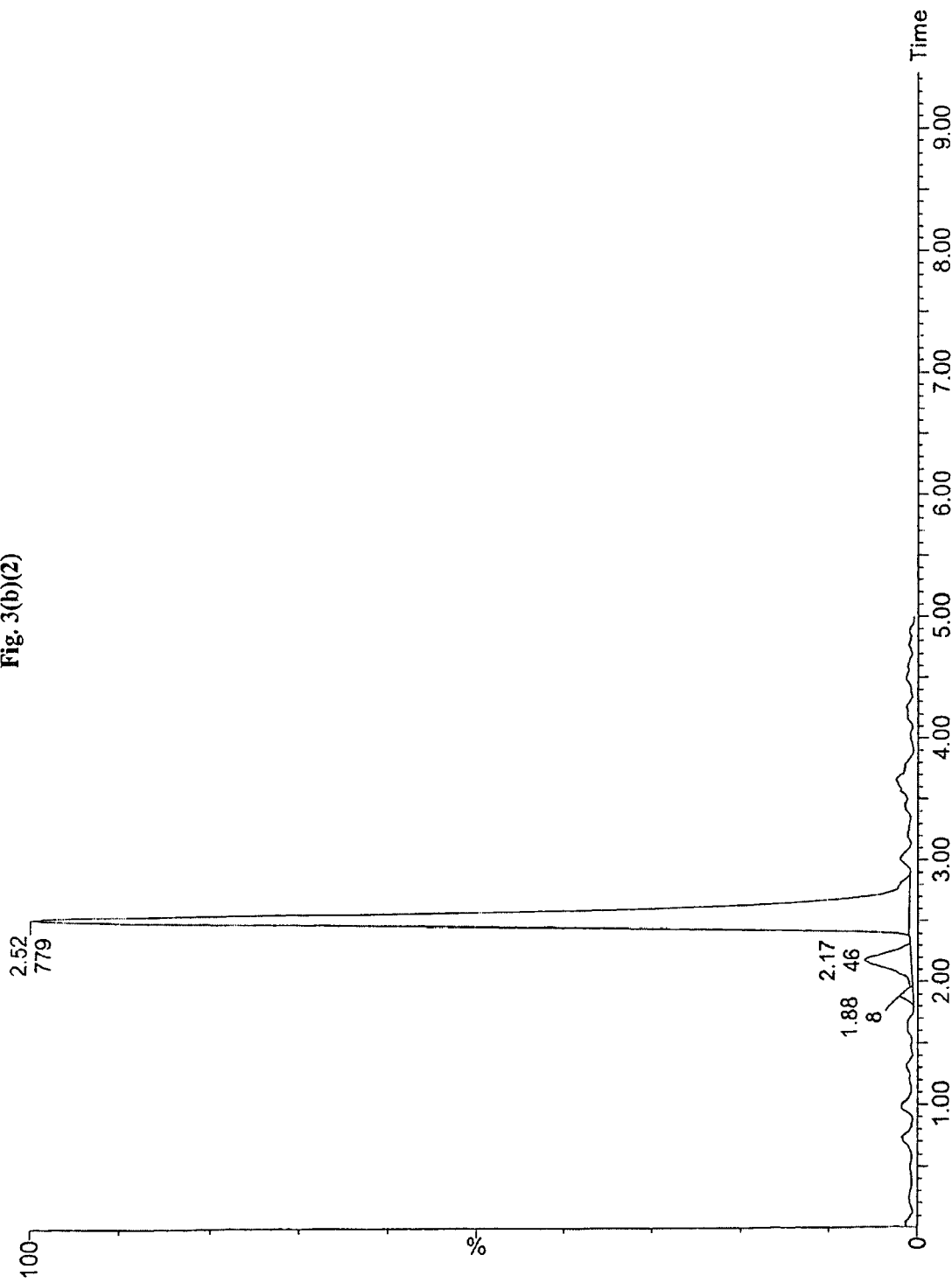
Fig. 3(b)(2)

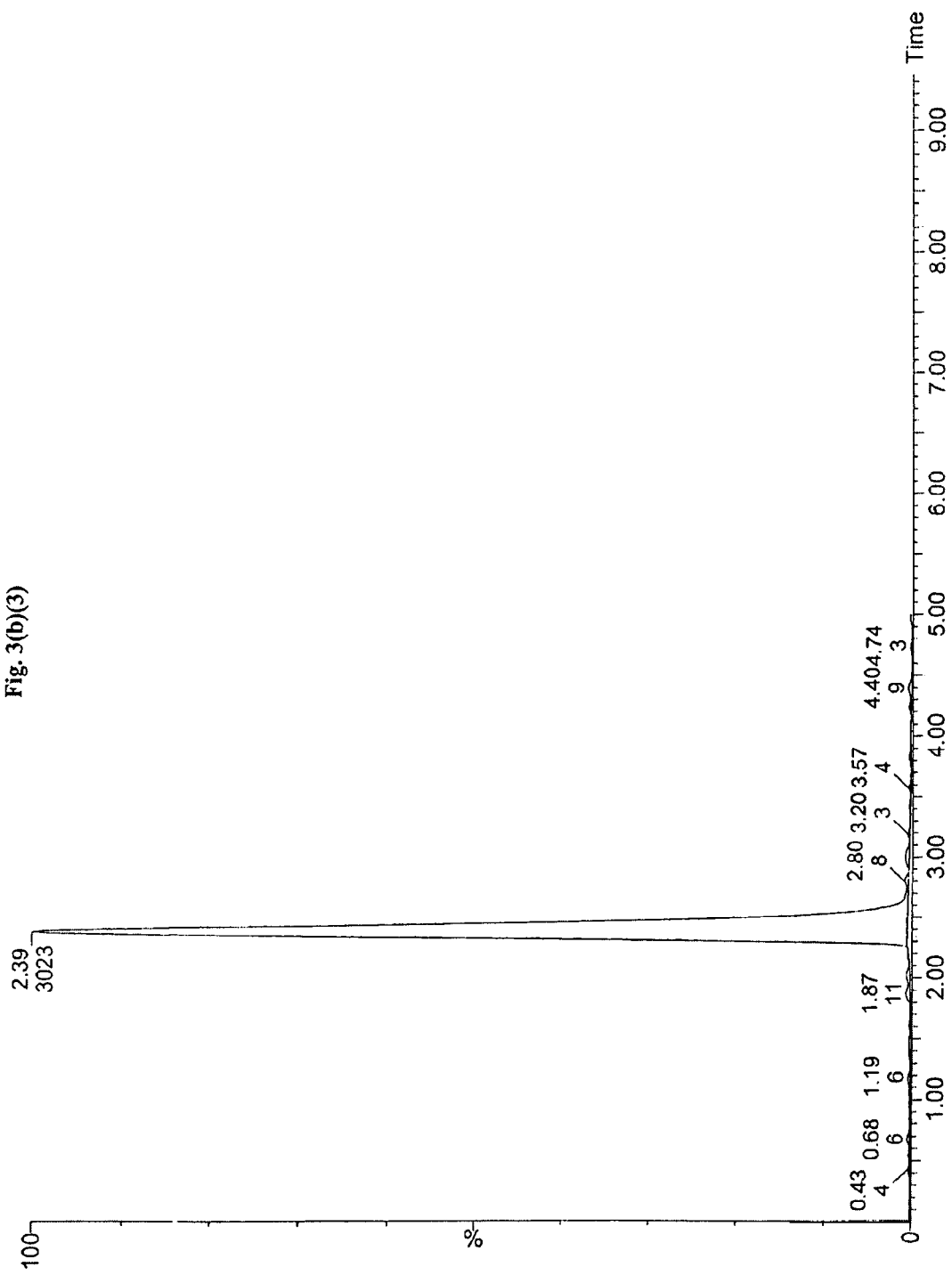

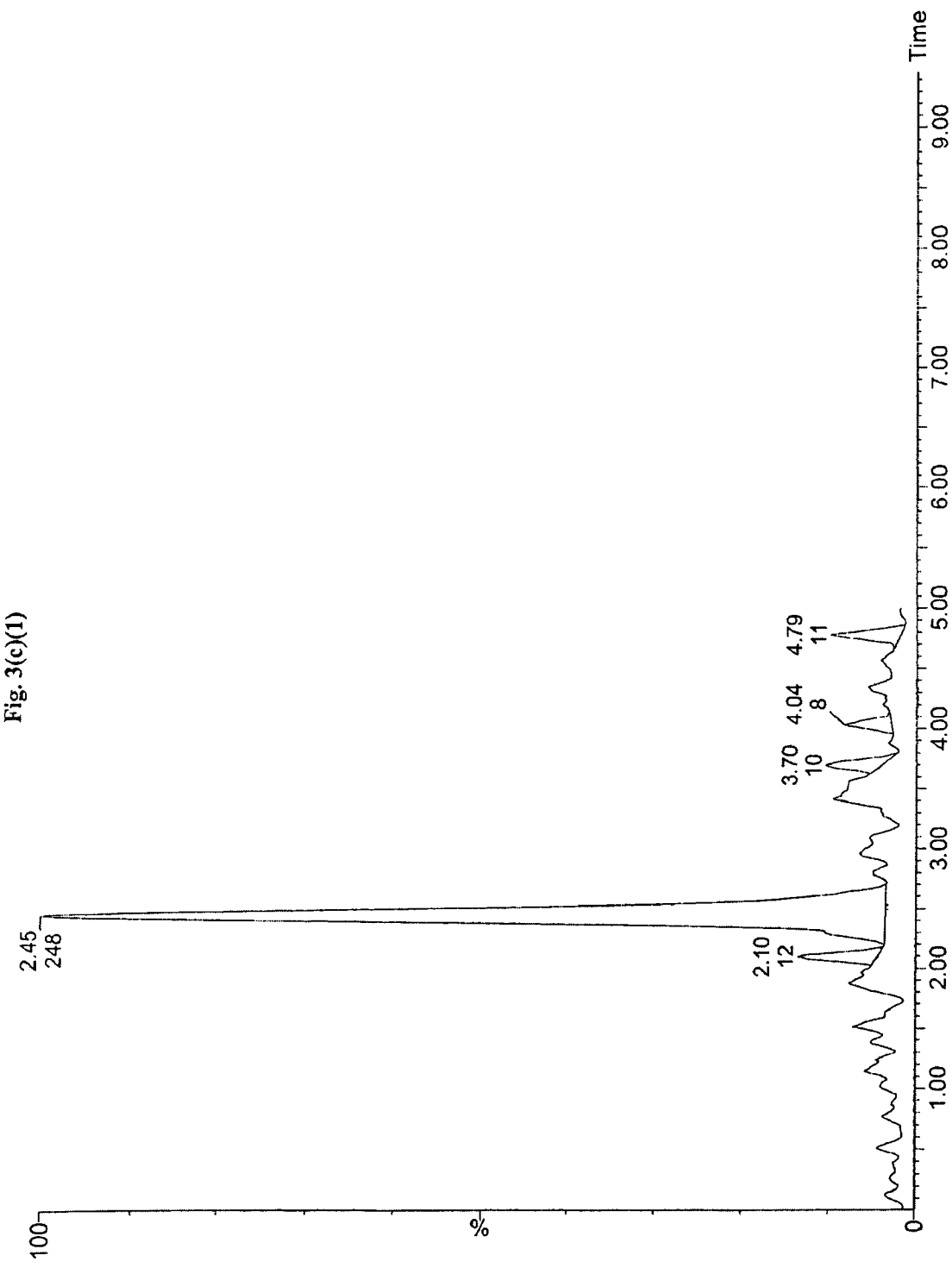

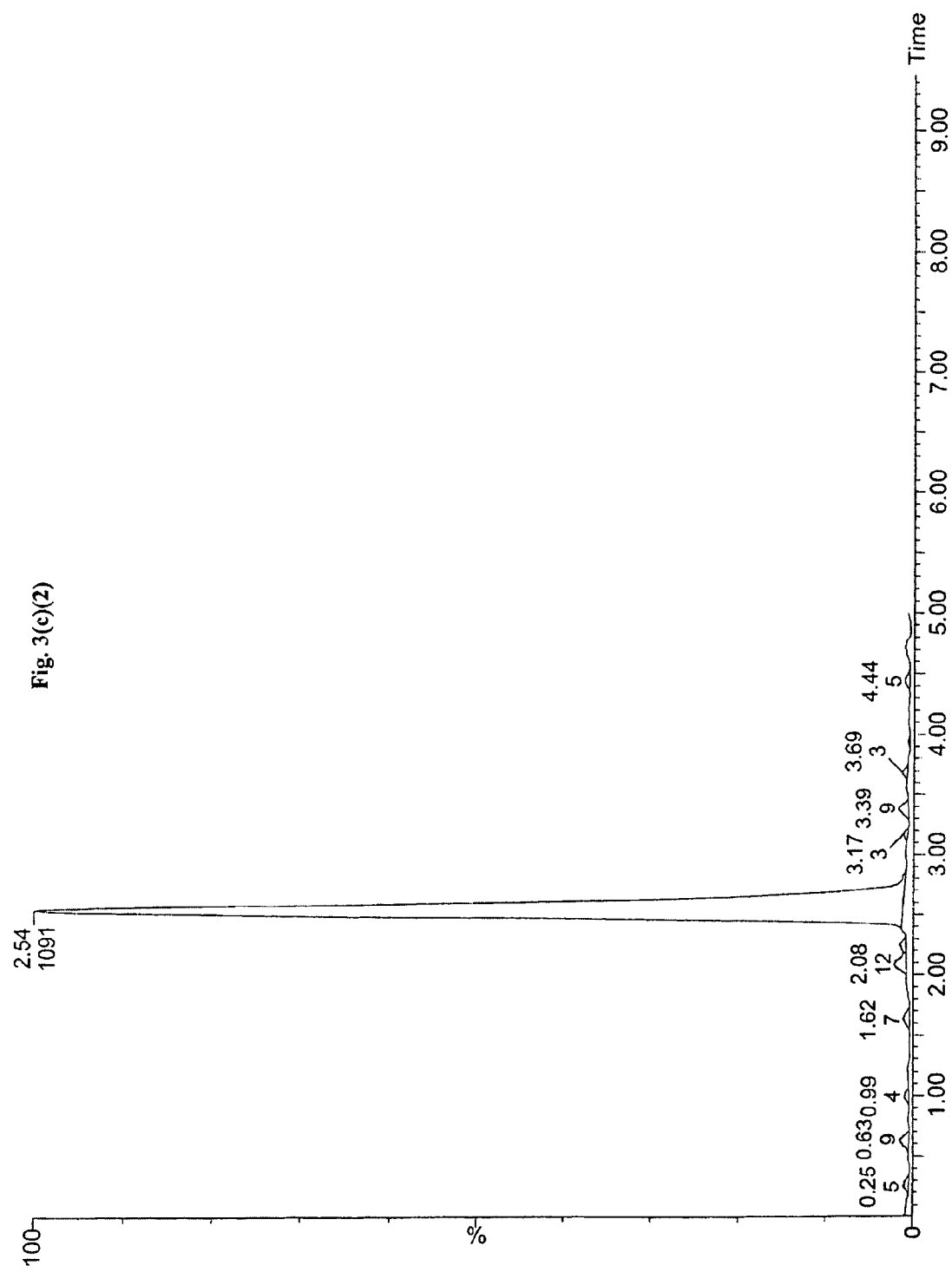

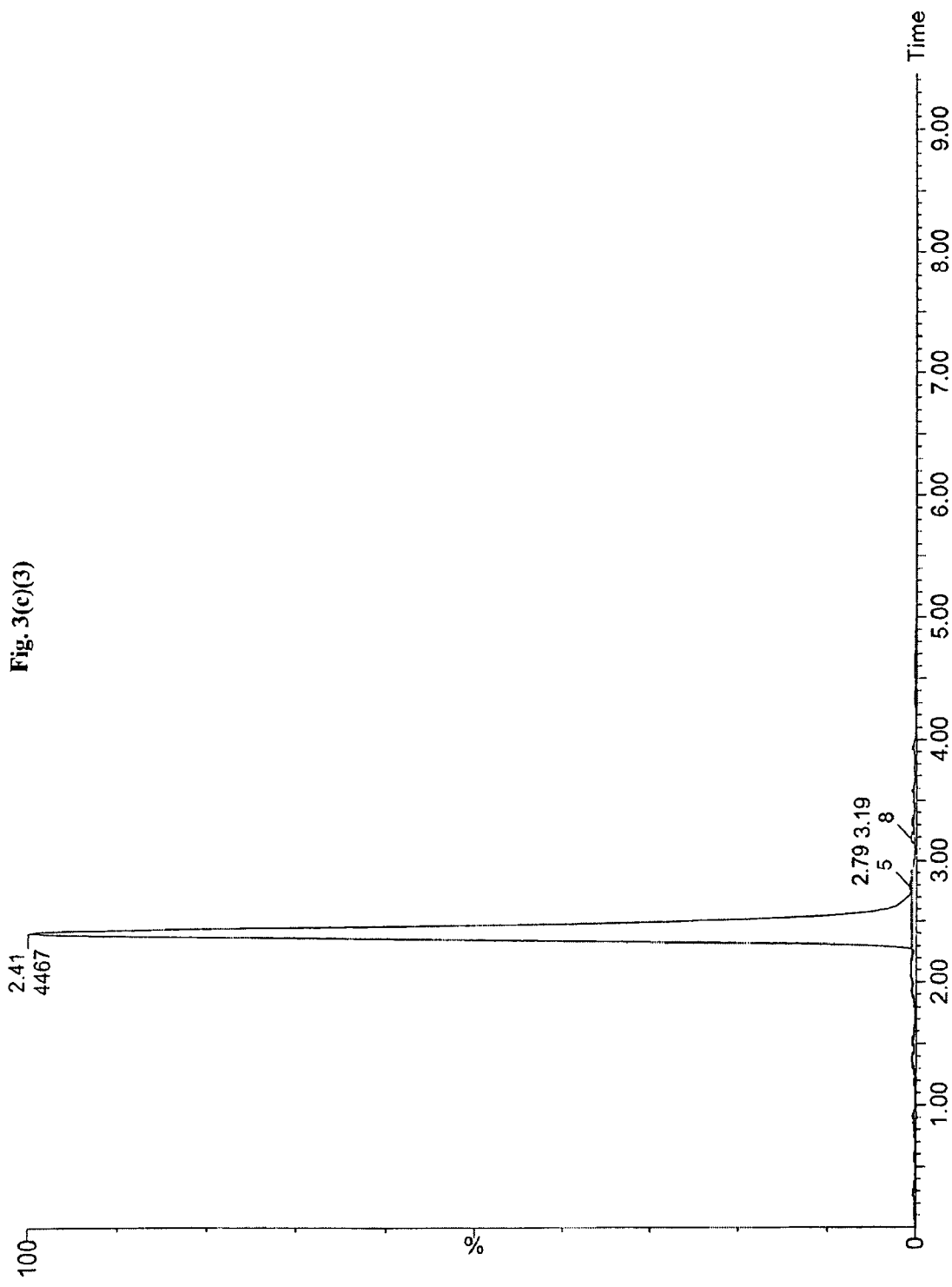
Fig. 3(c)(3)

Fig. 4
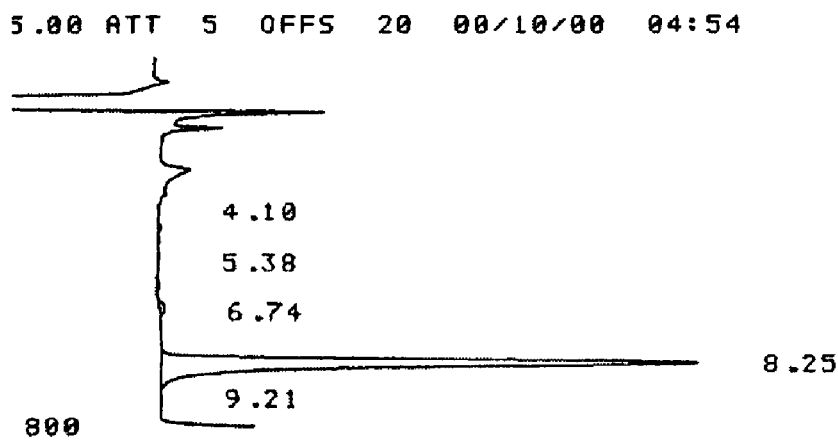
A
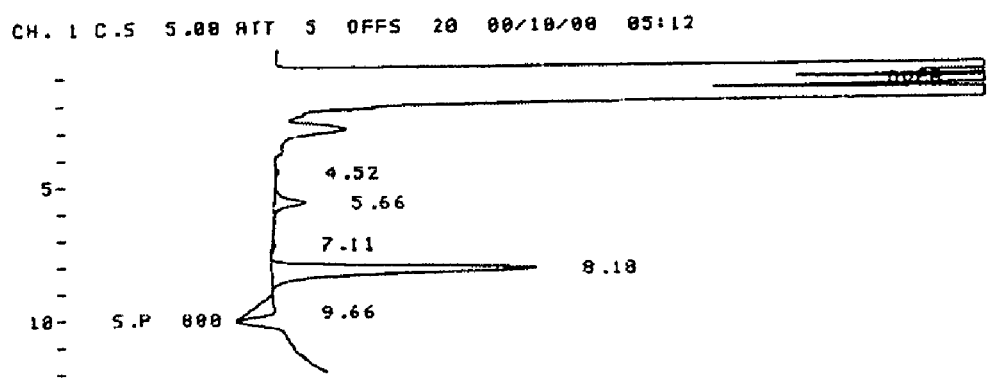
B

PREPARATION OF SAMPLES FOR LC-MS/MS USING MAGNETIC PARTICLES

RELATED APPLICATIONS

This application claims priority to EP 07011633.0 filed Jun. 14, 2007.

FIELD OF THE INVENTION

The invention is directed to the field of sample preparation for liquid chromatography-tandem mass spectrometry. Particularly, the invention concerns preparation procedures suitable for the detection of low molecular weight substances in complex biological samples such as plasma, serum, or whole blood.

BACKGROUND

Liquid chromatography (LC) is an extremely important analytical technique which is used for the separation, identification, and quantitation of an analyte of interest even if present in a complex mixture of different sample constituents. During LC the chemical components in a mixture were carried through a stationary phase by the flow of a liquid mobile phase. Separation in liquid chromatography is achieved by means of differences in the interactions of the analytes with both the mobile and stationary phases. As the skilled artisan appreciates, both a stationary phase and a mobile phase appropriate to the analytes under investigation have to be chosen. In addition, the user will identify chromatographic conditions appropriate to maintain the sharpness of analyte bands as a sample moves through the stationary phase column to the detector.

High performance liquid chromatography, also known as high pressure liquid chromatography, abbreviated as HPLC, is a special form of liquid chromatography and nowadays used frequently in biochemistry and analytical chemistry. The analyte is forced through a column of the stationary phase in a liquid (mobile phase) at high pressure which decreases the time the separated components remain on the stationary phase, and thus the time they have to diffuse within the column. This leads to narrower peaks in the resulting chromatogram and thence to better resolution and sensitivity as compared to LC.

The mobile phase is chosen to ensure solubility of the sample solutes. For the stationary phase, preferably microparticulate silica (bare or chemically modified) is used because its high surface area accentuates the differences in solute-stationary phase interactions. The use of a stationary phase that interacts strongly with solutes relative to solute mobile-phase interactions will result in very long retention times, a situation which is not analytically useful. Hence the stationary phase must be selected so as to provide weak to moderate solute interactions relative to those in the mobile phase. As a consequence, the nature of the solute governs the type of LC selected. The stronger interactions should occur in the mobile phase to ensure sample solubility and ready elution, while the stationary phase should be responsive to more subtle differences among the solutes. For example, polar neutral compounds are usually better analyzed using a polar mobile phase together with a nonpolar stationary phase that distinguishes subtle differences in the dispersive character of the solutes. One of the powerful aspects of HPLC is that the mobile phase can be varied to alter the retention mechanism. Modifiers can be added to the mobile phase to control retention. For example, pH is an important variable in aqueous mobile phases.

Five general classes of LC can be distinguished:
1. Normal-phase chromatography calls for the use of a polar stationary phase in conjunction with a non-polar (dispersive) mobile phase.
2. Reversed-phase chromatography, the opposite possibility, calls for the use of a non-polar stationary phase and a polar mobile phase (composed of one or more of the polar solvents, e.g., water, methanol, acetonitrile, and tetrahydrofuran).
3. Ion-exchange chromatography involves ionic interactions. In this case the mobile phase must support ionization to ensure solubility of ionic solutes. The stationary phase must also be partially ionic to promote some retention. Consequently, the interactions with the stationary phase are strong, and this is usually reflected in longer analysis times and broad peaks.
4. Size-exclusion chromatography involves separations based on molecular size alone and ideally requires that there be no energetic interaction of the solutes with the stationary phase.
5. Affinity chromatography is based on a specific interaction, e.g., between the members of a specific binding pair like antigen and corresponding antibody or receptor and corresponding ligand. For example, a first partner of a binding pair is bound to an appropriate stationary phase and used to capture the second partner of the binding pair. The second partner can be released and isolated by appropriate means.

The general classification of separation principles given above is not, exhaustive and therefore is non-limiting. There are other separation principles which can be used for the separation of liquid samples, e.g., hydrophobic interaction chromatography, hydrophilic interaction chromatography, ion-pair chromatography, and molecular imprinted materials based separation.

The analyte of interest can be detected by any appropriate means. Appropriate and preferred detectors sense the presence of a compound passing through and provide an electronic signal to a recorder or computer data station. The output is usually in the form of a chromatogram, and a substance of interest is usually found in a certain peak. The peak area or peak height can be used to quantify the amount of analyte present in the sample investigated.

The detector for an HPLC system is the component that emits a response due to the eluting sample compound and subsequently signals a peak on the chromatogram. It is positioned immediately posterior to the stationary phase in order to detect the compounds as they elute from the column. The bandwidth and height of the peaks may usually be adjusted using the coarse and fine tuning controls, and the detection and sensitivity parameters may also be controlled by the skilled artisan. There are many types of detectors that can be used with HPLC. Some of the more common detectors include: refractive index (RI), ultra-violet (UV), fluorescent, radiochemical, electrochemical, near-infra red (near-IR), mass spectrometry (MS), nuclear magnetic resonance (NMR), and light scattering (LS).

Refractive index (RI) detectors measure the ability of sample molecules to bend or refract light. This property for each molecule or compound is called its refractive index. For most RI detectors, light proceeds through a bi-modular flow-cell to a photodetector. One channel of the flow-cell directs the mobile phase passing through the column while the other directs, only the mobile phase. Detection occurs when the light is bent due to samples eluting from the column, and this is read as a disparity between the two channels.

Fluorescent detectors measure the ability of a compound to absorb then re-emit light at given wavelengths. Each compound has a characteristic fluorescence. The excitation source passes through the flow-cell to a photodetector while a monochromator measures the emission wavelengths.

Radiochemical detection involves the use of radiolabeled material, usually tritium (3H) or carbon-14 (14C). It operates by detection of fluorescence associated with beta-particle ionization, and it is most popular in metabolite research.

Electrochemical detectors measure compounds that undergo oxidation or reduction reactions. This is usually accomplished by measuring gain or loss of electrons from migrating samples as they pass between electrodes at a given difference in electrical potential.

Mass spectrometry is an analytical technique used to measure the mass-to-charge ratio (m/z or m/q) of ions. It is most generally used to analyze the composition of a physical sample by generating a mass spectrum representing the masses of sample components. The technique has several applications including identifying unknown compounds by the mass of the compound and/or fragments thereof determining the isotopic composition of one or more elements in a compound, determining the structure of compounds by observing the fragmentation of the compound, quantitating the amount of a compound in a sample using carefully designed methods (mass spectrometry is not inherently quantitative), studying the fundamentals of gas phase ion chemistry (the chemistry of ions and neutrals in vacuum), and determining other physical, chemical or even biological properties of compounds with a variety of other approaches.

A mass spectrometer is a device used for mass spectrometry, and it produces a mass spectrum of a sample to analyze its composition. This is normally achieved by ionizing the sample and separating ions of differing masses and recording their relative abundance by measuring intensities of ion flux. A typical mass spectrometer comprises three parts: an ion source, a mass analyzer, and a detector.

The kind of ion source is a contributing factor that strongly influences-what types of samples can be analyzed by mass spectrometry. Electron ionization and chemical ionization are used for gases and vapors. In chemical ionization sources, the analyte is ionized by chemical ion-molecule reactions during collisions in the source. Two techniques often used with liquid and solid biological samples include electrospray ionization (ESI) and matrix-assisted laser desorption/ionization (MALDI). Other techniques include fast atom bombardment (FAB), thermospray, atmospheric pressure chemical ionization (APCI), secondary ion mass spectrometry (SIMS), and thermal ionisation.

Liquid-chromatography-tandem-mass spectrometry (LC-MS/MS) has been introduced in clinical chemistry (Vogeser M., Clin. Chem. Lab. Med. 41 (2003) 117-126). Advantages of this technology are high analytical specificity and accuracy and the flexibility in the development of reliable analytical methods. In contrast to gas chromatography mass spectrometry (GC-MS) as the traditional mass spectrometric technology in clinical chemistry. LC-MS/MS has been shown to be a robust technology, allowing its application also in a large scale routine laboratory setting. Requirements for the preparation (clean-up) of sample material are limited compared to GC-MS; however, de-proteinizing is mandatory for small molecule target analyses.

Mere protein precipitation as presented by the state of the art may be sufficient for some LC-MS/MS methods, but in order to avoid ion-suppression effects for very sensitive methods, more efficient extraction methods are usually required (Annesley, T. M., Clin. Chem. 49 (2003) 1041-1044). "Off-line" or "on-line" solid phase extraction or solvent extraction are the techniques currently used to solve this problem. Respective time consuming manual sample preparation protocols so far represent an important limitation for the large scale routine application of LC-MS/MS in the clinical laboratory. Therefore, automation of sample preparation for LC-MS/MS is a goal that is addressed by application of different technical principles:

Samples can be loaded into 96-well plates to be submitted to batch protein precipitation by centrifugation (Vogeser, M. and Spöhrer. U. Clin. Chem. Lab. Med. 44 (2006) 1126-1130). This, however, is a discontinuous process since-plates have to be transferred into a centrifuge manually. Alternatively, filtration of precipitated samples using filtration plates and application of vacuum may be performed (Williams, M. G., et al., Biomed. Chromatogr. 17 (2003) 215-218). Mere protein precipitation, however, does not allow analyte concentration.

Solid phase extraction with extraction plates or single extraction cartridges allows full automation with a continuous work-flow from loading of samples until MS-analysis (Yang, L, et al., J. Chromatogr. B 809 (2004) 75-80; Alnouti, Y. et al., J. Chromatogr. A 1080 (2005) 99-106: Koal. T., et al., Clin. Chem. Lab. Med. 44 (2006) 299-305; Taming, J., et al., J. Pharm. Biomed. Anal. 41 (2006) 213-218.). In these methods, too, vacuum or positive air pressure has to be applied during extraction which is technically demanding.

The use of magnetic particles has been most successfully introduced to the automation of heterogenous immunoassays years ago (Porstmann, T. and Kiessig, S. T., J. Immunol. Methods 150 (1992) 5-21); respective particles used as the solid phase for extraction are ideally suited for automation, since this "solid phase" can be manipulated as a liquid. Today, this principle represents the predominant technology applied in a number automated immunoassay systems. Automated methods for DNA purification based on functionalized magnetic particles have been introduced to routine laboratories as well (Namvar, L., et al., J. Clin. Microbiol. 43 (2005) 2058-2064).

WO 2005/015216 and WO 2006/075185 disclose processes for the preparation of coated polymer particles containing superparamagnetic crystals. Porous, surface-functionalized particles are reacted with at least one polyisocyanate and at least one diol or at least one epoxide. WO 2005/015216 discloses that such beads are of utility in adsorption/desorption processes analogously to the mechanisms in (a) reversed phase chromatography or hydrophobic chromatography, and (b) hydrophobic interaction chromatography. Particularly, adsorption of a mixture of proteins to functionalized beads is described, followed by fractionation of the proteins by applying desorption buffers containing (a) increasing concentrations of acetonitrile and (b) decreasing concentrations of ammonium sulfate.

Functionalized magnetic beads for reversed phase magnetic isolation, desalting, concentration, and fractionation of complex peptide mixtures are commercially available under the trademark DYNABEADS (Dynal, Inc.) RFC18 from Invitrogen Corporation. According to the product description, magnetic separation allows fractionation of complex samples and the fractions can be applied to matrix assisted laser desorption ionization (MALDI) targets for MS analysis, or analyzed in other downstream applications such as electrospray-MS and HPLC.

Extraction protocols based on the use of magnetic particles have successfully been adapted for MALDI-TOF analyses. Zhang, X., et al., J. Biomol. Tech. 15 (2004) 167-175 disclose the processing of human plasma samples using a magnetic bead-based hydrophobic interaction chromatography resin. Villanueva, J., et al., Anal. Chem. 76 (2004) 1560-1570 disclose an automated sample preparation from human serum samples wherein peptides are captured and concentrated using a reversed-phase batch processing and magnetic particles which are surface-derivatized with reversed-phase ligands. However, the document also discloses that in some cases, prior to reversed-phase extraction, sera were additionally subjected to incubation with additives such as urea, DTT, or n-octylglucoside. Also, proteins were removed from sera by way of precipitation or filtration, or serum albumin was removed by affinity chromatography.

When considering quantitative testing, MALDI-TOF analysis has certain disadvantages. The sample material or a subtraction thereof has to be mixed with a solution of a matrix compound, and the mixture is applied to the target. After that the solvent is evaporated. Importantly, the evaporation process usually docs not lead to an even distribution of the analyte in the mixture on the target. Thus, depending on the particular spot hit by the laser beam in order to mobilize matrix and analyte material into the gas phase, the amount of analyte may differ from spot to spot. As a consequence, peak size does not reliably reflect the concentration of the analyte in the sample material or the subtraction thereof.

Aiming at quantitative detection by means of mass spectrometry, alternative ways to vaporize sample and/or analyte material are provided by atmospheric pressure ionization, e.g., electrospray ionization (ESI) or atmospheric pressure chemical ionization (APCI). However, prior to the analysis by mass spectrometry, the analyte to be quantitatively detected needs to be enriched or partially purified, particularly when the analyte is to be detected in complex sample material such as blood, serum, or plasma. To this end, the chromatographic separation step of LC-MS/MS is insufficient when performed alone. However, magnetic separation using beads with a functionalized hydrophobic surface prior to MS analysis is insufficient, too. This is especially true when quantitative analysis of analytes is intended.

When considering LC-MS/MS, in order to sufficiently reduce sample complexity and remove unwanted contaminants, the sample can be treated with a precipitant prior to the LC step to precipitate and subsequently remove, e.g., high molecular weight compounds such as proteins or carbohydrates. Also, a liquid/liquid extraction step is possible. Furthermore, the LC step can be designed as a 2-dimensional (2D) chromatography. In this case, a first chromatography using a first stationary phase is performed, and one particular fraction is subjected to a second chromatography, usually with a second stationary phase, before the analyte is injected into the MS/MS system. The theoretical solutions discussed here have disadvantages in that they are inconvenient, laborious, pose problems for automation and/or require sophisticated and expensive equipment.

The problem to be solved by the present invention was to improve sample preparation for quantitative target analysis of small molecule analytes with mass spectrometry means, that is, LC-MS/MS, whereby the analytes are extracted out of complex biological matrices like serum, plasma, whole blood, or lysed whole blood.

The analysis of peptides prepared from serum or plasma using hydrophobic magnetic particles as described in the state of the art basically targets molecules with a molecular weight greater than 700 Da (Daltons) and up to about 20,000 Da. In whole blood, plasma, and serum there is a plethora of compounds with a molecular weight below about 700 Da. Among these, peptides are just one group out of many others, including amino acids, lipids, and many different metabolites of the biochemical pathways. Thus, there exists a significant complexity of blood, plasma, and serum samples with regards to small (i.e., smaller than about 700 Da) molecular compounds.

The inventors unexpectedly found that the use of functionalized magnetic particles with a hydrophobic surface greatly enhances the process for extraction of small molecule analytes out of complex biological matrices such as whole blood, plasma, and serum. The magnetic particles according to the invention can reversibly bind low molecular weight compounds when the particles are added to the biological samples. A particular surprising finding was that the binding process is not disturbed when lipids, peptides, and proteins are abundantly present in the sample matrix. Another very surprising observation was that even very low amounts of functionalized magnetic beads are sufficient to extract and enrich low molecular weight compounds from complex sample matrices in a concentration-dependent manner. Thus, magnetic beads are much more convenient for reversed phase separation as opposed to stationary phases in the form of chromatography columns, which are much more prone to clogging when complex sample materials are processed.

The findings by the inventors proved to be especially advantageous when functionalized magnetic beads were used for the extraction of analytes from plasma, serum, and whole blood in which lipids, peptides, and proteins, among others, are particularly abundant. After the binding step and by separating the panicles with magnetic force from the remaining sample material, unbound components of the biological sample can be removed efficiently from the bound analytes. Elution of the analytes from the particles provides the desired low molecular weight compounds in a form which is sufficiently pure for analysis by mass spectrometry such as LC-MS/MS analysis. Even more surprising, functionalized magnetic particles with a hydrophobic surface can be used to extract small molecule analytes out of whole blood samples which, prior to extraction, were-subjected to hemolysis. Not only is the extraction (=sample preparation) procedure according to the invention suitable for qualitative detection of a desired analyte with a low molecular weight, surprisingly, the use of functionalized magnetic particles with a hydrophobic surface also allows quantitative detection of the analyte using mass spectrometry as a detection means.

SUMMARY OF THE INVENTION

A first aspect of the present invention is the use of functionalized magnetic particles with a hydrophobic surface for extracting a compound with a molecular weight between 50 and about 700 Da from a complex liquid biological sample. Another aspect of the invention is a method to purify a compound with a molecular weight between 50 and about 700 Da from a complex liquid biological sample, comprising the steps of (a) contacting the sample with an amount of functionalized magnetic particles with a hydrophobic surface, (b) incubating the sample and the particles, thereby adsorbing the compound to the hydrophobic surface, (c) separating the particles by applying a magnetic field and removing the liquid, (d) optionally washing the particles, (e) eluting the compound from the particles, whereby the particles/sample ratio is equal or greater than 1.25 mg/ml and the extraction efficacy for the compound is between about 40% and about 100%. A further aspect of the invention is a method to assay a compound with low molecular weight in a liquid biological sample by way of mass spectrometry, comprising the steps of (a) contacting the sample with an amount of functionalized magnetic particles with a hydrophobic surface, (b) incubating the sample and the particles, thereby adsorbing the compound to the surface, (c) separating the particles by applying a magnetic field and removing the liquid, (d) optionally washing the particles, (e) eluting the compound from the particles, (f) fractionating the eluate of step (e) by way of liquid chromatography, and (g) detecting the compound in a fraction obtained in step (f) by way of mass spectrometry. A further aspect of the invention is a porous magnetic particle with two different surfaces, characterized in that the first surface engulfs the pore lumen and is functionalized with a chemical group selected from the group consisting of a C4-C30 alkyl group, a copolymer of 1-vinylpyrrolidon and a comdivinylbenzene, and a copolymer of styrene and divinylbenzene, and the second surface is the remaining surface around the pores, whereby the second surface is either determined by the chemical composition of the solid phase or functionalized with a chemical group which is different from the chemical group on the first surface.

BRIEF DESCRIPTION OF THE FIGURES

FIGS. 1(a)-(d): Representative LC-MS/MS multiple reaction monitoring chromatograms obtained from different samples submitted to sample preparation
  (a): injection of pure solution of itraconazole, undiluted
  (b): injection of extract obtained from a pure solution of itraconazole (initial concentration 1,000 µg/l; tenfold dilution during extraction process)
  (c): injection of extract obtained from a serum sample spiked with itraconazole (initial concentration 1,000 µg/l; tenfold dilution during extraction process)
  (d): injection of material obtained by simple protein precipitation (state-of-the-art) with acetonitrile from a serum sample spiked with itraconazole (initial concentration 1,000 µg/l; tenfold dilution during extraction process)

FIG. 3(a)-(c): Representative LC-MS/MS multiple reaction monitoring chromatograms obtained from different patient whole blood samples submitted to sample preparation
  (a) containing Tacrolimus, representative results for
    (1) 2.1 µg/l,
    (2) 10.5 µg/l, and
    (3) 39.7 µg/l
  (b) containing Sirolimus
    (1) 2.1 µg/l,
    (2) 10.5 µg/l, and
    (3) 47.2 µg/l
  (c) containing Everolimus
    (1) 2.1 µg/l,
    (2) 11.7 µg/l, and
    (3) 43.9 µg/l FIG. 4: Representative LC-MS/MS multiple reaction monitoring chromatograms obtained from different patient serum samples submitted to sample preparation containing Mycophenolic acid. A standard; B patient sample.

DETAILED DESCRIPTION OF THE INVENTION

Figure 1A:
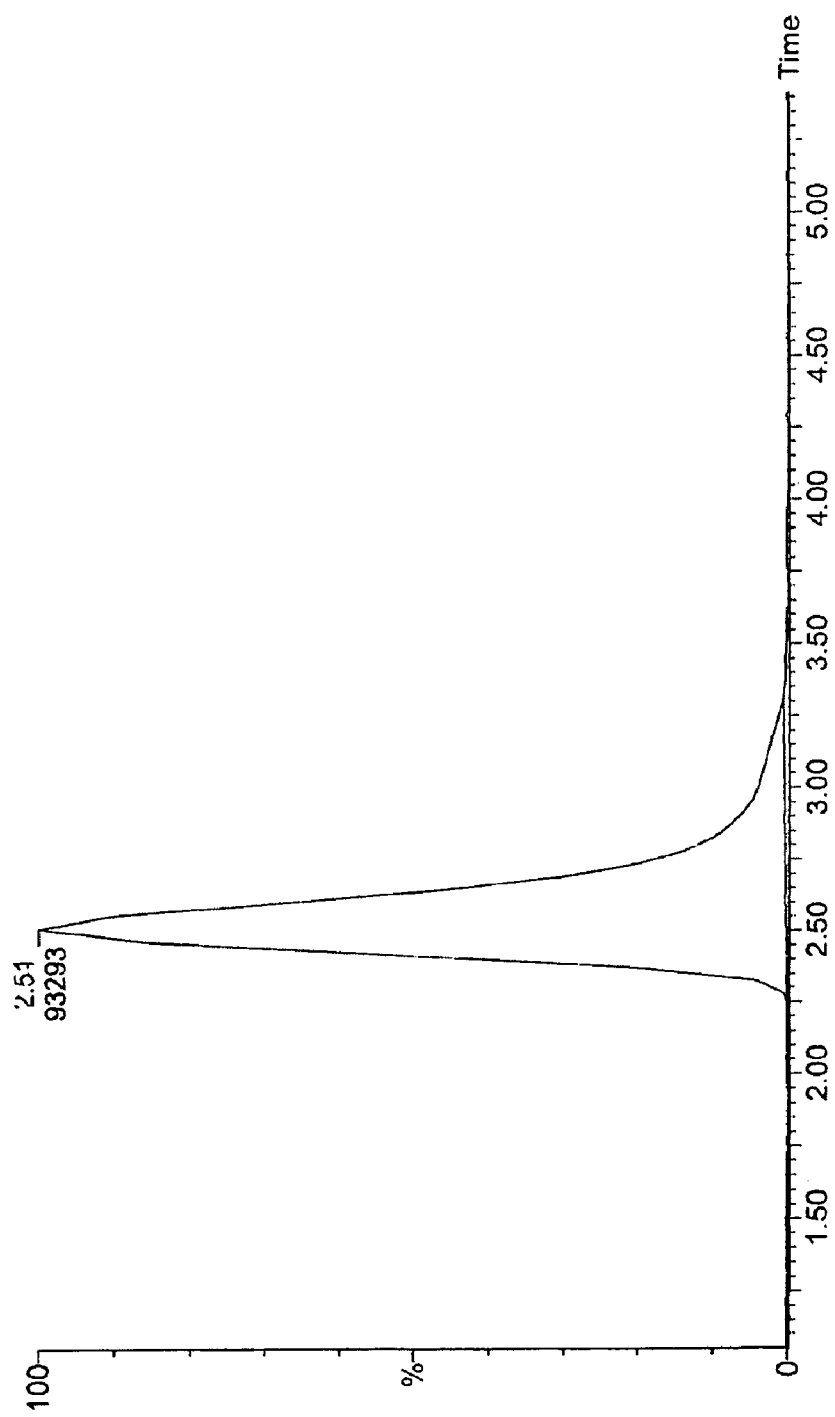
Figure 1B:
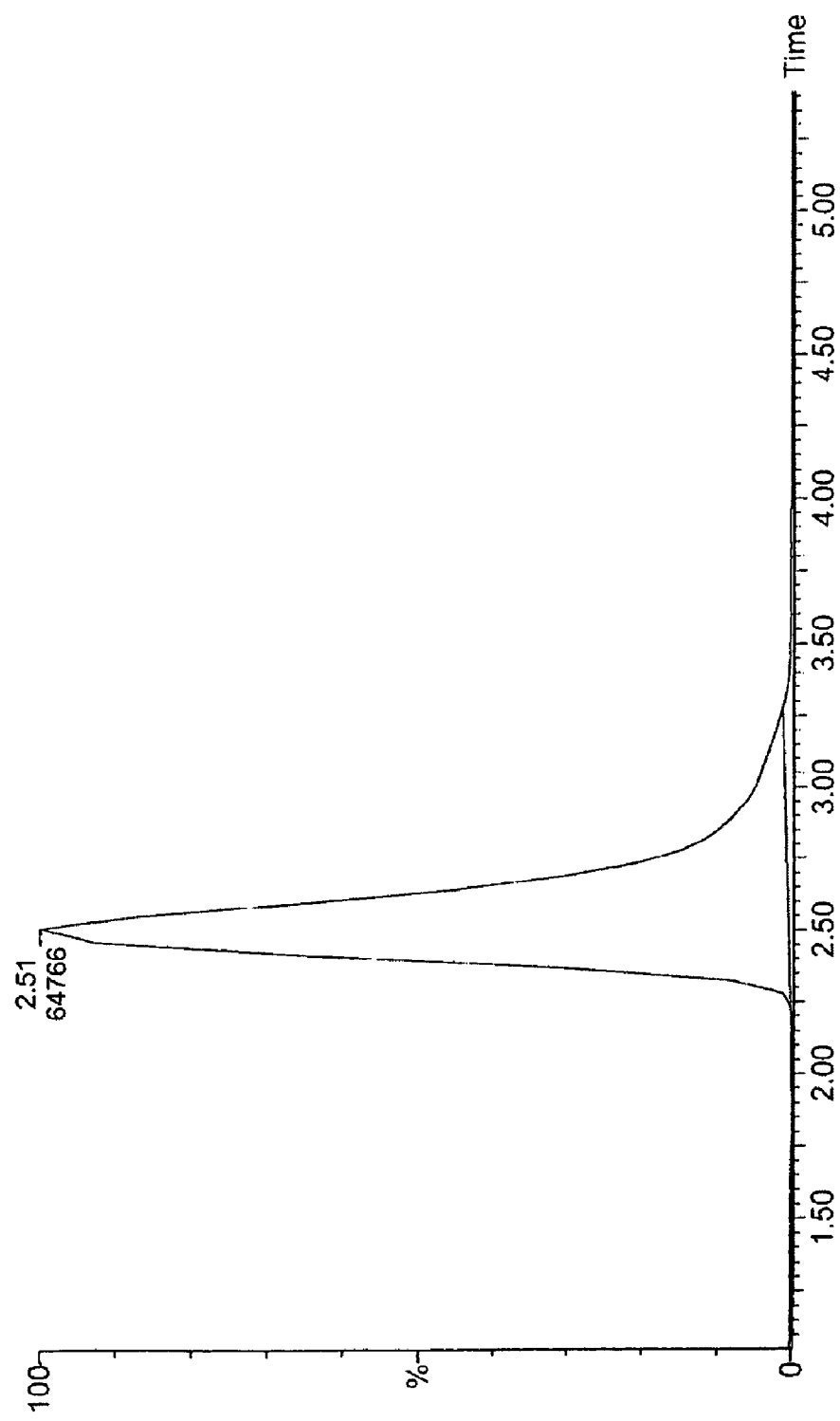
Figure 1C:
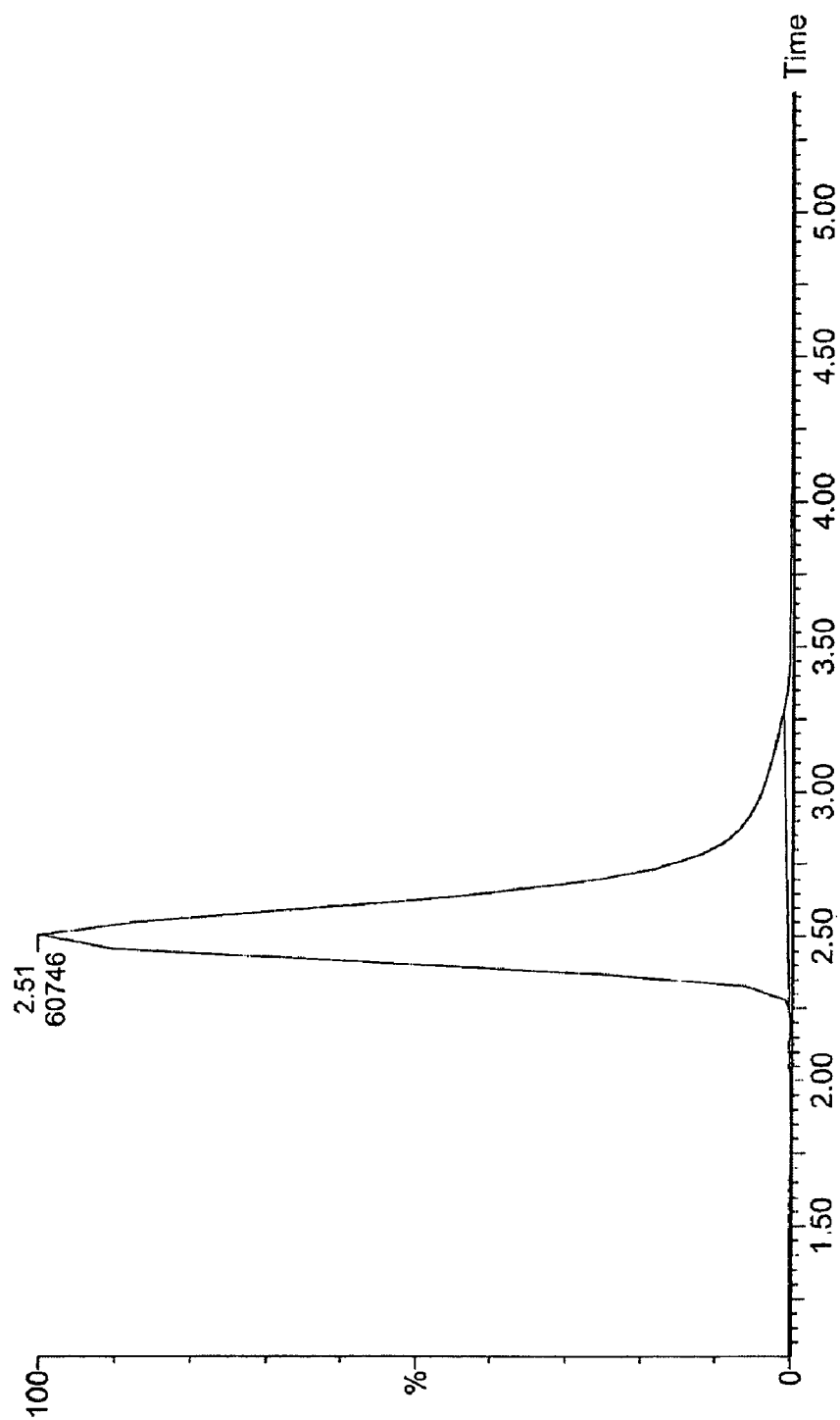
Figure 2:
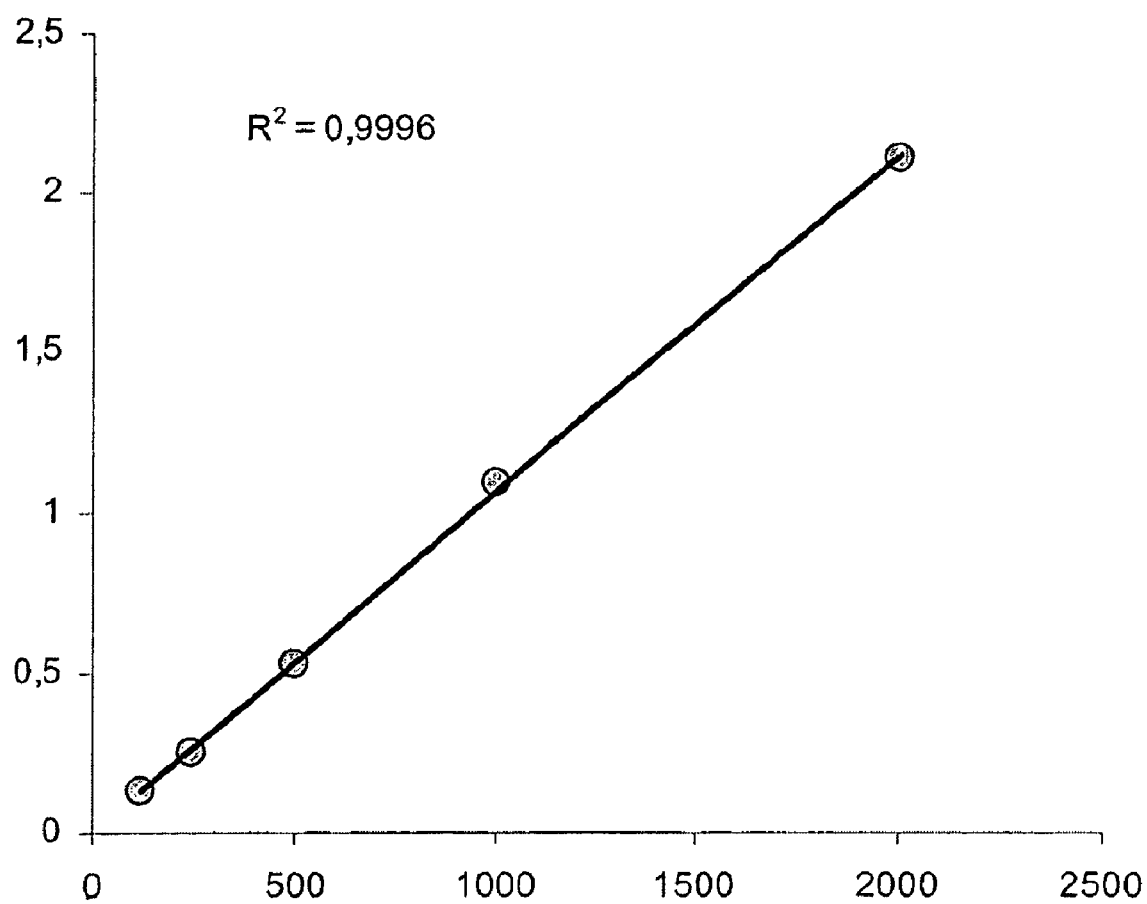
FIG. 2: Calibration line for measurement of itraconazole obtained from calibration materials submitted to sample preparation by microparticles. Ordinate: Response. LC-MS/MS; peak area itraconazole internal standard. Abscissa: Concentration in µg/l itraconazole.

Certain terms are used with particular meaning, or are defined for the first time, in this description of the present invention. For the purposes of the present invention, the following terms are defined by their art-accepted definitions, when such exist, except that when those definitions conflict or partially conflict with the definitions set forth below. In the event of a conflict in definition, the meaning of the terms are first defined by the definitions set forth below.

The term "comprising" is used in the description of the invention and in the claims to mean "including, but not necessarily limited to".

The articles "a" and "an" are used herein to refer to one or to more than one (i.e. to at least one) of the grammatical object of the article. By way of example, "a compound" means one compound or more than one compound.

When designating a range of numerical values such as a concentration range, the range is indicated by the word "between", followed by a first value n1 and a second value n2. The lower boundary of the designated range is understood as being the value equal to or higher than the first value. The higher boundary of the designated range is understood as being the value equal to or lower than the second value". Thus, a value x the designated range is given by $n1 \leq x \leq n2$.

Further, it is understood that the term "about" in combination with a numerical value n indicates a value x in the interval given by the numerical value ±5% of the value, i.e. $n-0.05*n \leq x \leq n+0.05*n$. In case the term "about" in combination with a numerical value n describes a preferred embodiment of the invention, the value of n is most preferred, if not indicated otherwise.

The present invention deals with enhancements of sample preparation prior to the detection of analytes which are low molecular weight (=LMW) compounds. One or more. LMW compounds can be present in the sample to be analyzed. A "low molecular weight compound" "small molecule", or a "molecule", "substance" or "compound" of "low molecular weight" is a molecule which exhibits a molecular weight of less than 5,000 Da (Da=Daltons), preferably less than 2,000 Da, more preferably less than 1,000 Da, most preferably less than 500 Da.

A compound or a composition is a "liquid" if at room temperature and normal atmospheric pressure the compound is in the "liquid" state and forms a liquid phase.

The terms "aqueous", "aqueous" phase and "aqueous" solution describe a liquid phase of which the solvent portion comprises water. However, other solvents such as a water-miscible organic cosolvent can be present in the solvent portion, too. In view of the presence of a cosolvent a solution is considered "aqueous" when between 30% and 100%, measured as volume by volume [volume by volume], of the solvent portion is water.

The term "sample" (or "sample material") as used herein refers to a mixture of compounds in which the analyte to be determined can be present and from which it can be purified, if present. The skilled person will find the invention to be particularly advantageous when the sample is a complex sample. A complex sample contains a plurality of organic and inorganic compounds which are desired to be separated from the analyte to be targeted, when the analyte is present in the sample. Usually, the sample is a biological sample. The sample preferably may comprise any body fluid. Preferred test samples include blood, blood serum (=serum), blood plasma (=plasma), urine, saliva, sputum, cerebral fluid or synovial fluid. Other samples are samples of in vitro eel) culture constituents, homogenates of bacteria, animal, plant or fungal cells or tissue, and cleared supernatants thereof.

Very much preferred samples are whole blood, serum, and plasma, with plasma or serum being most preferred. The blood plasma is preferably EDTA, heparin, or citrate blood plasma.

According to the invention, a preferred biological sample is a liquid sample which, however, may contain cellular or other particulate material, e.g., whole blood. Other preferred liquid samples are serum and plasma.

As the skilled artisan will appreciate, any assay using material from the sample is made in vitro. The patient sample is discarded or stored afterwards. The patient sample is solely used for the in vitro method of the invention and the material of the patient sample is not transferred back into the patient's body.

Furthermore, a lysate of biological material or a cleared supernatant thereof is encompassed by the term "sample". A "lysate" can be obtained from sample such as material comprising tissue, cells, bacteria or viruses, whereby the structural integrity of the material is disrupted, e.g., by adding an organic solvent and/or a detergent and/or a chaotropic salt, or by applying an osmotic shock. The term "lysate" does not encompass treatment with a hydrolase enzyme such as a protease or a nuclease.

The term "solid phase" is understood as being a substrate which is insoluble in the aqueous and non-aqueous liquids with which the present invention is practiced.

The term "magnetic particle" denotes a particle with paramagnetic or superparamagnetic properties. That is to say, the particle is magnetically displaceable but does not retain any magnetisation in the absence of an externally applied magnetic field. Examples for magnetic particles and methods for producing them can be found in WO 2005/015216 as well as in the references cited in this document. Particularly preferred is a magnetic polymer particle which contains paramagnetic or superparamagnetic crystals. The surface of a magnetic polymer panicle can be modified chemically.

The terms "functionalize" and "functionalization" as used herein relate to chemical modification of a solid phase (substrate) to provide a plurality of functional groups on the substrate surface. By a "functionalized surface" as used herein is meant a substrate surface that has been modified so that a plurality of functional groups are present thereon. The chemical modification of the solid phase comprises one or more chemical (functional) groups which are covalently linked to the solid phase or integral part of the solid phase. The functional groups are capable of mediating a physical interaction of an analyte with the solid phase, such that the analyte is bound non-covalently and reversibly. An example for a functional group is a hydrophobic group.

The term "biologically active compound" denotes a synthetic or non-synthetic substance which produces an effect on living matter or alters a function of living matter when contacted therewith. The term excludes compounds which are nutrients. Biological activity is usually dosage-dependent. A prominent kind of biological activity is a substance's toxicity.

The commonly accepted meaning of "LC-MS/MS" is liquid chromatography-tandem mass spectrometry. For LC-MS/MS liquid chromatographic separation, such as by high pressure liquid chromatography (HPLC) or another LC system, is combined on-line with mass spectrometry (MS) to result in enhanced sensitivity and specificity. In LC-MS/MS, the effluent from an HPLC is directed towards the inlet to the MS. Mass spectrometers can be of different types like quadrupol instruments (single quadrupol or triple quadrupol), time of flight instruments, ion trap instruments or hybrid instruments (example quadrupol—time of flight). Compounds eluting from the LC system are analyzed in real time as they elute. Two types of scans can be performed. One type measures the masses of the intact species eluting from the LC system. This can be done by scanning over a broad mass range (example 100 to 2,000 m/z) or by scanning one, two or several individual masses of interest (selected ion monitoring=SIM). A second type of measurement is using gas phase fragmentation. Fragmentation can be performed in the ion source (e.g., electrospray, ESI or atmospheric pressure chemical ionisation, APCI), this is known as "in-source fragmentation". Fragmentation can be preferably performed after isolation of one or more specific precursor ions in a tandem MS. After fragmentation specific fragment ions are measured. This type of measurement is known as multiple reaction monitoring=MRM or, selected reaction monitoring=SRM. MRM type of measurement ensures the highest sensitivity and specificity.

An exemplary technical problem underlying the present invention arises when complex samples containing an abundance of proteins are to be prepared, for an assay by LC-MS/MS for LMW compounds as analytes. Conventionally, single samples a simple protein precipitation is performed. While the precipitation removes unwanted components from the liquid phase, the desired analyte remains in solution. However, the precipitation step necessitates a subsequent centrifugation step, or an equivalent means to separate the precipitate from the liquid phase (supernatant), before the latter can be processed and analyzed further. Particularly a centrifugation step results in a discontinous process. Having full automation of the sample preparation workflow in mind, the inventors set out to develop alternative and more advantageous solutions.

The inventors discovered that functionalized magnetic particles provide unexpected benefits in the workflow of sample preparation preceding the analysis of a LMW compound from complex liquid samples. Thus, a first aspect of the present invention is the use of functionalized magnetic particles with a hydrophobic surface for extracting a compound with low molecular weight from a complex liquid biological sample. In a preferred embodiment of the invention, the functionalized surface comprises one or more hydrophobic groups. In a very much preferred embodiment the particle/sample ratio is higher than 0.1 mg/ml and lower than 100 mg/ml. Even more preferred, the particle/sample ratio is higher than 1 mg/ml.

With great advantage, the method of the invention results in reduced ion suppression which has a positive impact on the quality of mass spectrometric analysis, e.g. by LC-MS/MS. In addition, the workflow using functionalized magnetic particles according to the invention leads to an increased purity of the analyte from the sample material. As a consequence, HPLC separation is less demanding with respect to separation efficiency, thereby reducing costs and increasing speed of the analytical process. At the same time, the lifetime of the analytical HPLC columns is increased.

Very surprisingly, when comparing similarly functionalized chromatographic material and magnetic beads using an amount of about 100 μg of functionalized magnetic beads with a hydrophobic surface analytes such as biologically active compounds and metabolites thereof could be recovered from a 10 μl sample of whole blood, plasma or serum. Even more surprising, the extraction efficacy for the analyte was about 70% or higher.

Therefore in an even more preferred embodiment of the invention, the particles/sample ratio is equal or greater than 1.25 mg/ml and the extraction efficacy for the compound is between about 40% and about 100%. Even more preferred, the particles/sample ratio is equal or greater than 3.1 mg/ml and the extraction efficacy for the compound is between about 57% and about 100%. Even more preferred, the particles/sample ratio is equal or greater than 6.25 mg/ml and the extraction efficacy for the compound is between about 64% and about 100%. Even more preferred, the particles/sample ratio is equal or greater than 9.4 mg/ml and the extraction efficacy for the compound is between about 70% and about 100%. Even more preferred, the particles/sample ratio is equal or greater than 12.5 mg/ml and the extraction efficacy for the compound is about 100%.

Very much preferred, the functionalized magnetic particles with a hydrophobic surface are used for the extraction of a compound with a molecular weight between 50 Da and 1,000 Da. More preferred, the molecular weight of the compound is between 50 Da and 800 Da. Even more preferred the molecular weight of the compound is between 100 Da and 500 Da.

The technical effects of the present invention are also of general importance with respect to the goal of fully automated LC-MS/MS methods, since the inventors demonstrate for the first time the applicability of a magnetic particle based extraction protocol to small analyte quantitative LC-MS/MS target analysis. The particle technology offers substantial advantages compared to solid phase extraction protocols which involve "immobile" extraction materials: minimized handling of solid consumables (cartridges, plates); minimized volumes of liquid extraction solutions; and in particular no technically demanding application of vacuum or pressure to the extraction materials.

Another aspect of the invention is a method to purify a low molecular weight compound from a complex liquid biological sample, comprising the steps of (a) contacting the sample with an amount of functionalized magnetic particles with a hydrophobic surface, (b) incubating the sample and the particles, thereby adsorbing the compound to the hydrophobic surface, (c) separating the particles by applying a magnetic field and removing the liquid, (d) optionally washing the particles, (e) eluting the compound from the particles. Preferably, the low molecular weight compound is a compound with a molecular weight between 50 and about 700 Da.

The procedure of step (c), that is separating the magnetic particles from the remaining liquid phase is well known to the skilled person. E.g., by way of applying the magnetic field, the particles can be attracted to the wall of the container which holds the liquid sample and the magnetic particles. The liquid phase can then be aspirated, thereby separating the particles with any material adsorbed thereto from the remaining components of the sample. Subsequently, the particles can be washed with a washing buffer. The composition of the washing buffer is to be chosen such that the desired analyte remains bound to the particles.

Suitable and preferred particles to practice the present invention are magnetic nanoparticles and polymer particles containing magnetic pigment particles. However, other particles are possible. A further preferred particle is a porous particle which provides more than one functionalized surface and which provides restricted access to one particular functionalized surface. Very much preferred, the particles have a functionalized surface with one or more hydrophobic group to result in a hydrophobic surface area.

Magnetic particles (nanoparticles) with a hydrophobic surface can be generated by chemically coupling hydrophobic groups to $Fe_3O_4$, gamma-$Fe_2O_3$, mixed oxides of $Fe_2O_3$ and oxides of bivalent or trivalent metal ions, or mixtures thereof. To this end, procedures are disclosed in WO 00/26927 and elsewhere. In an alternative approach, polymer particles which contain paramagnetic or superparamagnetic crystals, can be prepared as described in WO 2005/015216 and WO 2006/075185. In these cases the modification chemistry targets the polymer. Styrenedivinylbenzene copolymers can be activated e.g. using 1,4-butanediol diglycidylether and glycidol. Remaining epoxy functional groups can be modified using e.g. alkylalcohols. Alternatively, commercially available epoxy modified magnetic styrenedivinylbenzen copolymers (e.g., DYNABEAD M270 epoxy, Invitrogen Corporation, 1600 Faraday Ave, Carlsbad, Calif. 92008, catalogue no. 143-01) can be used.

Very much preferred, the hydrophobic group with which the surface or part of the surface of the solid phase is functionalized is selected from the group consisting of an aliphatic linear, branched or cyclic saturated or unsaturated hydrocarbon residue, and an aromatic organic residue, whereby the aromatic residue may also comprise a heterocyclic residue.

According to the invention, the surface of the magnetic particles is even more preferably functionalized with C4-C30 alkyl residues, more preferred C8-C25, even more preferred C18. Other preferred hydrophobic particles are for example copolymers of 1-vinyl-pyrrolidone and divinylbenzene, and styrene and divinylbenzene, respectively.

The solid phase of the magnetic particles can be a porous or non-porous solid phase. A preferred porous solid phase has an average pore size of about 50 to 1000 nm, more preferred about 50 to 300 nm, even more preferred about 200 nm. Most preferred, the solid phase is functionalized exclusively on the surface surrounded by the pore lumen. Using such a porous solid phase, also known as "restricted access material", the simultaneous function of a molecular sieve can be achieved, in addition to the interaction between the analyte and the functionalized surface. That is to say, higher molecular compounds are excluded from access to the pore lumen due to steric hinderance, and therefore from interacting with the functionalized surface of the solid phase.

The procedure according to the invention is particularly advantageous for the separation of a biologically active LMW compound from a liquid biological sample.

Preferably, the liquid sample is selected from the group consisting of whole blood, serum, and plasma. In addition and more preferred, the liquid sample can be hemolyzed blood, that is to say a blood sample in which the integrity of cellular constituents has been disrupted. E.g., erythrocytes in a blood simple can be lysed by applying an osmotic shock.

When using magnetic particles with a hydrophobic surface a preferred LMW compound has some lipophilic character and is capable of interacting directly with the hydrophobic surface. Alternatively, the LMW compound is capable of participating in hydrophobic interactions upon addition of ion pairing reagents.

In this context, lipophilic character means, the LMW compound shows a high binding affinity to the hydrophobic surface of the magnetic beads in an aqueous solution with high water content and this binding can be released by lowering the water content and increasing the organic content of the solution.

By way of example, a water content of between 100% and 90% is considered to be an aqueous solution with a high water content. Increasing in this solution the concentration of a water-miscible organic solvent such as methanol from 10% to 80% results in an aqueous solution with a low water content.

In this context, other organic solvents could be acetonitrile, ethanol or other aliphatic alcohols or other water-miscible organic compounds like dimethylformamide (DMF) or dimethylsulfoxide (DMSO). Ion pairing reagents could be for example trifluoroacetic acid, ammonium salts or sulfonium salts.

Particularly, the invention is practiced to purify biologically active LMW compounds, e.g. from complex liquid samples such as body fluids. Very much preferred biologically active LMW compounds are organic compounds which are soluble in matrices with high water content, e.g. in whole blood or serum, and which are also soluble in mixtures of water and organic solvents.

Solubility of a LMW compound can be influenced by the pH of the solution if protonation and deprotonation of the LMW compound is possible.

Typical LMW compounds for which the invention is very much suited are pharmaceutical compounds. There is particular utility for immunosuppressives such as rapamycin, tacrolimus, mycophenolic acid, everolimus, sirolimus, and metabolites thereof. Other very much preferred LMW compounds are endogeneous metabolites such as folic acid, vitamins, and hormones.

A further preferred target analyte according to the present invention is a drug of abuse. A drug of abuse is preferably selected from the group consisting of amphetamine, cocaine, and cocaine metabolites like benzoylecgnonine, methamphetamine, opiate and opiate derivatives, cannabinoids like tetrahydrocannabinol, and phencyclidine. A further preferred target analyte is folate especially the total folate as comprised in both the blood plasma and in the red blood cells. Well-known immunosuppressive drugs are, e.g., mycophenolate mofetil (MMF), rapamycin (RAPA also known as sirolimus), and tacrolimus (FK-506). Therapeutic drug monitoring for immunosuppressive drugs is especially important for transplant patients as well as for patients suffering from AIDS (cf., e.g., Drug Ther. Perspect 17(22) (2001) 8-12). Most patients who undergo solid organ transplantation require lifelong immunosuppressive therapy to prevent allograft rejection. Because, many immunosuppressive agents have narrow therapeutic ranges and are associated with various toxicities and the potential for drug interactions, the use of therapeutic drug monitoring (TDM) in conjunction with clinical assessment of patients is particularly important.

Therefore, an immunosuppressive drug as a preferred analyte is selected from the group consisting of cyclosporine (CsA), mycophenolate mofetil (MMF), rapamycin (RAPA also known as sirolimus), tacrolimus (FK-506) azathioprine (AZA), and methylprednisolone (MP).

Also preferred is a target analyte that is present in a red blood cell. Preferred analytes to be measured from a differentially hemolyzed whole blood sample are sirolimus, tacrolimus and folate.

Mycophenolate mofetil is a prodrug. After oral administration, mycophenolate mofetil (MMF) undergoes rapid hydrolysis in the intestine and blood to form its active metabolite mycophenolic acid (MPA). MMF is widely available and is approved in the US and UK for the prevention of renal, hepatic or cardiac allograft rejection in combination with corticosteroids and cyclosporin. The drug has demonstrated superiority over azathioprine in reducing the incidence of acute rejection of renal allografts. The therapeutic trough concentration is in the range of 1-3.5 mg/l. MMF can be measured from plasma and from whole blood.

Tacrolimus is a macrolide antibiotic that was first approved by the US Food and Drug Administration (FDA) in 1994 for the prevention of liver allograft rejection. It is up to 100 times more potent than cyclosporin in vitro, and clinically, it is associated with a greater reduction in the incidence of tissue rejection. Tacrolimus has demonstrated efficacy both as primary immunosuppressive therapy in patients undergoing various transplantation procedures, and as rescue therapy for patients with refractory acute allograft rejection after liver or kidney transplantation. The therapeutic trough concentration is in the range of 5-20 µg/i.

Since at least part of the tacrolimus present in the circulation is compartmented within erythrocytes, a whole blood sample is used in the clinical routine measurement of this drug. Tacrolimus can e.g. be detected by high performance liquid chromatography (HPLC), HPLC mass spectrometry (MS), radio receptor assay (RRA), or by an immunoassay (IA). The latter two methodologies do not detect tacrolimus and certain of its various metabolites with the same sensitivity. This may lead to an interference in the procedure used (Murthy, J. N., et al., Clin. Biochem. 31 (1998) 613-617). At least in the detection of the various tacrolimus metabolites the HPLC-MS-procedure may be considered the gold standard. All the procedures mentioned above, however, require the extraction of tacrolimus from whole blood. Usually acetonitrile is used in clinical routine for the extraction of tacrolimus from whole blond and no method appears to exist that would allow for an online measurement of tacrolimus from a whole blood sample.

Sirolimus is, like tacrolimus, a macrolide antibiotic. It was first approved in 1999 by the US FDA for the prevention of allograft rejection after kidney transplantation, and indeed has shown promising results in this respect when used acutely in combination with cyclosporin and corticosteroids. In vitro, sirolimus is up to 100 times more potent than cyclosporin, and clinically, it may exhibit synergism with cyclosporin, perhaps permitting a reduction in cyclosporin dosage. The therapeutic trough concentration is in the range of 5-15 µg/l.

As for tacrolimus, a significant amount of sirolimus is present within erythrocytes. Therefore extraction of a whole blood sample is required no matter which detection method is used. In clinical routine a sample suspected to comprise sirolimus is subjected to HPLC and sirolimus is detected by ultraviolet light (UV) or by MS/MS. Recently also a microparticle enzyme immunoassay has been described (Jones, K., et al., Clinical Therapeutics 22/suppl. B (2000) B49-B61).

Folate is the collective name of a group of related molecules differing in oxidation state. Folates are part of the water-soluble vitamin B group and are important as coenzymes for homocysteine metabolism and in the transfer of one-carbon groups required for DNA replication. Inadequate folate status is related to increased risk of neural tube defects, is associated with cardiovascular disease, anemia, with certain cancers and with Alzheimer's disease. Serum or plasma folate concentrations reflect recent dietary intake, whereas erythrocyte folate concentrations are more indicative of body stores (Gunter, E. W., et al, Clin. Chem. 42 (1996) 1689-1694; Fazili, Z., et al, Clin. Chem. 51 (2005) 2318-2325; Pfeiffer, C. M., et al, Clin. Chem. 50 (2004) 423-432). Erythrocyte total folate (red blood cell folate=RBC-folate) is the best measure of whole body folate status. Recent studies have shown that 5-methyl tetrahydrofolate is the dominant folate vitamer in circulating erythrocytes. For the diagnosis of folate deficiency it is recommended that determinations are performed not only from serum or from, plasma but also from erythrocytes, since folate is localized to more than 95% in the latter. The concentration in the erythrocytes more truly reflects the actual folate status.

A further surprising finding was that the purification method according to the invention, when used for sample preparation, provides a LMW compound in a suitable form for analysis by means of liquid chromatography and mass spectrometry. Another aspect of the invention is therefore a method to assay a compound with low molecular weight in a liquid biological sample by way of mass spectrometry, comprising the steps of (a) contacting the sample with an amount of functionalized magnetic particles with a hydrophobic surface, (b) incubating the sample and the particles, thereby adsorbing the compound to the surface, (c) separating the particles by applying a magnetic field and removing the liquid, (d) optionally washing the particles, (e) eluting the compound from the particles, (f) fractionating the eluate of step (e) by way of liquid chromatography, and (g) detecting the compound in a fraction obtained in step (e) by way of mass spectrometry. Preferably, the low molecular weight compound is a compound with a molecular weight between 50 and about 700 Da.

In step (g) the compound is preferably detected by LC/MS. A more preferred way of analyzing the eluate, however, is achieved using liquid chromatography-tandem mass spectrometry (LC-MS/MS).

The sample preparation method described here was found to result in very pure extracts obtained from human sample materials. As an effect, analytical interferences are reduced when applying liquid chromatography-tandem mass spectrometry. Ion suppression represents the most relevant analytical interference of liquid chromatography-mass spectrometry (LC-MS). Ion suppression results from the presence of an excess of non-target analyte matrix molecules in the ion source during ionization. Ion suppression effects compromise with lower concentration limits of quantification in LC-MS methods and therefore limit the applicability of LC-MS in the field of in-vitro diagnostics in general. Ion suppression can have differential impact on the ionization yield obtained for an target analyte and its individual internal standard compound, respectively. Since the severity of ion suppression may differ substantially between samples (in particular between calibration samples and patients' samples) inaccuracy can arise from ion suppression.

An essential advantage of the sample preparation technique described herein is the option of full automation of all steps included in the extraction process. In particular when combined with the technique of liquid-chromatography tandem-mass spectrometry (LC-MS/MS) this enables the development of dedicated analytical instrument for use in routine clinical laboratories. Introduction of unprocessed samples to an instrument today are a prerequisite for the application of analytical platforms in the clinical laboratory. This can be achieved with the sample preparation technique described here. A further prerequisite is a high throughput capacity of the analytical platform with short, analytical run times and highest analytical specificity. Respective features are best realized by LC-MS/MS, in particular when compared with single stage LC-MS and MALDI-TOF techniques.

In a preferred embodiment the detecting of an analyte using a method according to the present invention is performed by mass spectrometry. Compared with other detection techniques mass spectrometry gives highest specificity especially if combined with tandem mass spectrometry. With tandem mass spectrometry detection is a two dimensional process The following examples and figures are provided to aid the understanding of the present invention, the true scope of which is set forth in the appended claims. It is understood that modifications can be made in the procedures set forth without departing from the spirit of the invention.

EXAMPLE 1

Analysis of Itraconazole from Serum

For the demonstration of the invention the antimycotic drug itraconazole (CAS Registry/EC Number (RN) 84625-61-6) was used as a first representative small molecule target analyte.

In an exemplary case commercially available C18-functionalized magnetic particles (=beads) (Dynal DYNA-BEADS RPC18 (Prod. No. 102.01), Invitrogen, Karlsruhe, Germany; 50 mg/ml, mean particle diameter 1 μm) were used. The beads have a surface modified with C18 alkyl groups. Such particles were so far specified for the preparation of serum samples for MS-based protein analyses.

Serum samples from human patients were extracted using magnetic particles. In general the standard handling protocol given by the manufacturer was followed. 15 μl of the resuspended particles were transferred into 1.5 ml standard polypropylene reaction tubes placed in a magnetic particle separator (Dynal MPC-S Magnetic Particle Concentrator, Product No. 120.20, Invitrogen). A permanent magnet was introduced into the separator device, leading to immobilization of the beads on the wall of the tubes. The particle free liquid was removed with a pipette; then, the magnet was removed from the separator device.

For conditioning of the beads, 250 μl of 0.1% [volume by volume] trichloroacetic acid was dispensed into the tubes; the bead pellets were re-dissolved by multiple pipetting the liquid within the rubes. The magnet was applied again and trichloroacetic acid was removed. This conditioning step was repeated. The conditioned beads were resuspended in 50 μl of formic acid (0-1% [volume by volume]); 15 μl of the internal standard solution (R51012 (Vogeser, M., et al. Clin. Chem. Lab. Med. 41 (2003) 915-920), 1,000 μg/l in methanol/water (1/1 volume parts)) and 15 μl of serum were added. With a pipette the content of the tubes was aspirated and blown out several times for mixing, Adsorption of the analytes to the beads was allowed for two minutes. The sample matrix was removed with a pipette after again applying the magnet. Beads were washed two times with each 250 μl of water. After the second washing step the beads were resuspended in 75 μl of acetonitrile and 75 μl of formic acid (0.1% [volume by volume]) for analyte elution. After two minutes, the beads were captured magnetically and the supernatants were transferred into HPLC vials. The entire extraction procedure was performed at ambient temperature. LC-MS/MS analysis of the extract was performed as described previously (Vogeser, M., et al. Clin. Chem. Lab. Med. 41 (2003) 915-920) here using a Waters Micromass Quattro Ultima Pt instrument.

EXAMPLE 2

Recovery Rate of the Extraction Procedure for Itraconazole and Ion Suppression Properties To investigate the recovery fate of the extraction procedure and to characterize ion suppression properties of the entire analytical method, pure-solutions of itraconazole (1,000 μg/l and 100 μg/l, respectively, in methanol/water (10/90 [volume by volume]), and a serum sample spiked with itraconazole to a concentration of 1,000 μg/l were used. Injection of 7× of the pure solution with a concentration of 100 μg/l resulted in a peak area in the MRM trace of itraconazole of 80,978 (mean of three injections). The pure solution with a concentration of 1,000 μl was submitted to particle based extraction and 7 μl of the extract were injected. A mean peak area of 67,765 was observed. Since the extraction protocol includes a sample dilution by a factor of 10, these results correspond to an extraction recovery rate of 84%. The itraconazole spiked serum sample was extracted in the same way; and a mean peak area of 61,124 was observed, which was 9% less than found for the pure solution with the identical analyte concentration. This slightly lower signal may result from a lower recovery rate of the extraction method when applied to serum or to an ion suppression effect caused by residual serum matrix, or from a combination of both. For comparison, the spiked serum sample was precipitated with acetonitrile (100 μl sample, 900 μl acetonitrile); a mean peak area of 49,095 was observed. Thus the overall extraction efficacy (including recovery rate and ion suppression effects) of the bead based protocol was found superior compared to protein precipitation.

EXAMPLE 3

Validation with Samples from Itraconazole-Treated Patients

A validation protocol was performed in three independent analytical series. In each series a five-point calibration was performed using a commercially available calibration material for itraconazole measurement (2,000 µg/l, 1,000 µg/l, 500 µg/l, 250 µg/l, and 125 µg/l; Recipe, Munich, Germany). Aliquots of pooled serum from itraconazole treated patients were analyzed in triplicate in each series to calculate a total coefficient of variation (n=9). Commercially available quality control materials (ClinCheck, Recipe, Munich, Germany) in two concentration ranges (target concentrations 150 µg/l, and 2,900 µg/l) were analyzed in the three series.

Linear calibration lines (r>0.99) were obtained in all series. For the pooled serum a total coefficient of variation of 3.4% was observed (mean concentration 380 µg/l); all quality control samples were found within the predefined accepted ranges (±10% of the target concentrations).

EXAMPLE 4

Analysis of Blood Samples Containing Immunsupressiva

For the demonstration of the invention patient whole blood samples from patients treated with immunosupressant drugs were used as analytes. Immunosupressant drugs analysed were tacrolimus, sirolimus and everolimus.

In an exemplary case commercially available C18-functionalized magnetic particles (=beads) (Dynal DYNABEADS RPC18 (Prod. No. 102.01), Invitrogen, Karlsruhe, Germany; 50 mg/ml, mean particle diameter 1 µm) were used. The beads have a surface modified with C18 alkyl groups. Such particles were so far specified for the preparation of serum samples for MS-based protein analyses.

Whole blood samples from human patients were extracted using magnetic particles. In general the standard handling protocol given by the manufacturer was followed. 50 µl of the resuspended particles were transferred into 1.5 ml standard polypropylene reaction tubes placed in a magnetic particle separator (Dynal MPC-S Magnetic Particle Concentrator, Product No. 120.20, Invitrogen). A permanent magnet was introduced into the separator device, leading to immobilization of the beads on the wall of the tubes. The panicle free liquid was removed with a pipette; then, the magnet was removed from the separator device.

For conditioning of the beads, 250 µl of 0.1% [volume by volume] trichloroacetic acid was dispensed into the tubes; the bead pellets were re-dissolved by multiple pipetting the liquid within the tubes. The magnet was applied again and trichloroacetic acid was removed. This conditioning step was repeated. The conditioned beads were resuspended in 50 µl of formic acid (0.1% [volume by volume]); 50 µl of the internal standard solution and 50 µl of whole blood sample were added. With a pipette the content of the tubes was aspirated and blown out several times for mixing. Adsorption of the analytes to the beads was allowed for two minutes. The sample matrix was removed with a pipette after again applying the magnet. Beads were washed two times with each 250 µl of water. After the second washing step the beads were resuspended in 100 µl of methanol in water (90+10). After two minutes, the beads were captured magnetically and the supernatants were transferred into HPLC vials. The entire extraction procedure was performed at ambient temperature. LC-MS/MS analysis of the extract was performed as described previously (Vogeser, M., Spöhrer, U., Clin. Chem. Lab. Med. 44 (2006) 1126-1130) using a Waters Micromass Quattro Ultima Pt instrument.

Typical chromatograms are shown in FIG. 3.

EXAMPLE 5

Analysis of a Serum Patient Sample Containing Mycophenolic Acid

For the demonstration of the invention patient serum samples from patients treated with mycomophetilphenolat drugs were used as analytes. Mycophenolic acid (MPA) as active metabolite of mycomophetilphenolat was used as analyte and determined by HPLC-UV.

In an exemplary case commercially available C18-functionalized magnetic particles (=beads) (Dynal DYNABEADS RPC18 (Prod. No. 102.01), Invitrogen, Karlsruhe, Germany; 50 mg/ml, mean particle diameter 1 µm) were used. The beads have a surface modified with C18 alkyl groups. Such particles were so far specified for the preparation of serum samples for MS-based protein analyses.

Whole blood samples from human patients were extracted using magnetic particles. In general the standard handling protocol given by the manufacturer was followed. 50 µl of the resuspended particles were transferred into 1.5 ml standard polypropylene reaction tubes placed in a magnetic particle separator (Dynal MPC-S Magnetic Particle Concentrator, Product No. 120.20, Invitrogen). A permanent magnet was introduced into the separator device, leading to immobilization of the beads on the wall of the tubes. The particle free liquid was removed with a pipette; then, the magnet was removed from the separator device.

For conditioning of the beads, 250 µl of 0.1% [volume by volume] trichloroacetic acid was dispensed into the tubes; the bead pellets were re-dissolved by multiple pipetting the liquid within the tubes. The magnet was applied again and trichloroacetic acid was removed. This conditioning step was repeated. The conditioned beads were resuspended in 50 µl of formic acid (0.1% [volume by volume]); 50 µl of the internal standard solution and 50 µl of whole blood sample were added. With a pipette the content of the tubes was aspirated and blown out several times for mixing. Adsorption of the analytes to the beads was allowed for two minutes. The sample matrix was removed with a pipette after again applying the magnet. Beads were washed two times with each 250 µl of water. After the second washing step the beads were resuspended in 100 µl of methanol in water (90+10). After two minutes, the beads were captured magnetically and the supernatants were transferred into HPLC vials. The entire extraction procedure was performed at ambient temperature. LC-MS/MS analysis of the extract was performed as described previously (Vogeser M, et al.) using a HPLC-UV instrument.

Typical chromatograms are shown in FIG. 4.

EXAMPLE 6

Preparation of Hydrophobized Magnetite Nanoparticles

In general, preparation of ferrofluids was performed according to U.S. Pat. No. 3,843,540 and Ramirez, L. P., et al., (Macromol. Chem. Phys. 204 (2003) 22-31).

14.6 g ferric chloride and 12 g of ferrous chloride terrahydrate were dissolved in 50 ml distilled water and 40 ml of ammonium hydroxide solution was added. After co-precipitation of magnetite nanoparticles, oleic acid (45% [weight by weight] with respect to the magnetite) was added and the suspension was heated to 70° C. for 30 min. After that, the temperature was increased to 110° C. in order to evaporate water and excess of ammonia. The sediment was called to room temperature and was washed several times with distilled water.

EXAMPLE 7

Preparation of Water-based Ferrofluid

In general, preparation of ferrofluids was performed according to U.S. Pat. No. 3,843,540 and Ramirez, L. P., et al., (Macromol. Chem. Phys. 204 (2003) 22-31).

5 g of the magnetite powder from Example 6 (Preparation of hydrophobized magnetite nanoparticles) was added to 30 g of octane. This dispersion was poured into a solution consisting of 120 g water and SDS (12% [weight by volume] with respect to the dispersed phase consisting of octane, magnetite and oleic acid). The suspension was mixed for 1 h and sonicated with a UP200s (Dr. Hielscher GmbH) in an ice cooled bath. Octane was evaporated at 80° C. and water was added from time to lime to compensate the co-evaporated water.

EXAMPLE 8

Preparation of Polystyrene Based Seed Latex Particles 6 g SDS was dissolved in 475 ml water and stirred at 225 r.p.m. in a reaction vessel. The solution was degassed with nitrogen. 26 ml styrene was added and the resulting emulsion was stirred for 50 min at 80° C. in an argon atmosphere. 25 ml of an aqueous sodium hydrogen carbonate solution (10% [weight by volume]) was added. The solutions was stirred for additional 10 min. the polymerization reaction was initiated by adding 2.5 ml of ammonium peroxo disulfate solution (326 mg in 2.5 ml degassed water). After 4 h at 80° C., 3 M hydrochloric acid was added to neutralize the pH. The suspension was filtered hot. The solid content was adjusted to 4% [weight by volume].

EXAMPLE 9

Preparation of Magnetic Particles by Seeded Growth Polymerization

Step 1: 3 ml Toluene were dispersed with 152.4 mg bisbenzoyl peroxide in 30 ml aqueous SDS solution (0.25% [weight by volume]. 1 ml of the seed latex particles from Example 8 (Preparation of polystyrene based seed latex particles) was added and the dispersion was stirred for 24 h.

Step 2: 2 ml of hexadecane. 10 ml of water and 30 mg of SDS were homogenized to an emulsion. To this emulsion, 125 ml of the ferrofluid from Example 7 (Preparation of water-based ferrofluid) was added and mixed with the dispersion from step 1 in a reactor.

Step 3: 5.8 g Cyclohexanol, 3.75 g glycidylmethacrylate and 2.5 g ethylene glycol-dimethacryl are were dispersed in 50 ml aqueous SDS (0.25% [weight by volume]) and was stirred at room temperature for 3 hours. The resulting dispersion was added the dispersion of step 1 and stirred for additional 24 h at room temperature A solution of 2 g PVA (Erkol W 25/140) in 50 ml water was added and the reaction mixture was degassed for 20 min using nitrogen. The polymerization was done at 70° C. for 24 h. The resulting precipitate was washed twice in water and methanol.

EXAMPLE 10

Pore Size Specific Hydrolysis and C8-Surface Modification 0.5 g of the particles from Example 9 (Preparation of magnetic particles by seeded growth polymerization) were treated for 48 h with 10 ml aqueous polystyrene sulfonic acid (1% [weight by volume]). The product was filtered and washed several times with water to neutralize the pH.

The particles were added to a solution of 14 mg-potassium hydroxide in 3.5 g hot octanol. The reaction was done for 10 hours at 70° C. The reaction mixture was diluted with 20 ml dioxane and cooled to room temperature The particles were filtered and washed several times with water.

The product was redisperged in 10 ml 0.1 N sodium hydroxide solution and stirred for 15 h at room temperature to inactivate remaining epoxy functional groups. The filtered product was washed with water and redispersed in destilled water to a solid content of 2% [weight by volume].

EXAMPLE 11

Comparison of the Recovery Rates Achieved with Protein Precipitation, Solid Phase Extraction, and by Using C18-Functionalized Magnetic Particles Analysis of different solutions and extracts containing the example analyte itraconazole was performed with LC-MS/MS; the respective peak areas of the MRM (multiple reaction monitoring) trace of itraconazole were recorded. Sample 1 was a pure solution of 200 µg/l itraconazole in a 9/1 (ratio of volume parts) mixture of methanol/formic acid (0.1% [v/v]). Sample 2 was obtained from a plasma sample with an itraconazole concentration of 2,000 µg/l by protein precipitation with methanol/acetonitrile (9/1 ratio), whereby 100 µl sample were mixed with 900 µl precipitation mix; the precipitate was pelleted by centrifugation for 12 min with 16,000 g. Sample 3 was obtained from a plasma sample with an itraconazole concentration of 2,000 µg/l by solid phase extraction with a commercially available C18 extraction column (ISOLUTE C18, Biotage AB) containing 100 mg extraction material. The columns were equilibrated with each 1 ml of water followed by methanol; 100 µl of the plasma sample was loaded; the column was washed with 1 ml of water; for analyte elution 1 ml of methanol/formic acid (0.1%) (9/1) was applied. The samples 4-1 to 4-5 were prepared from a plasma sample with an itraconazole concentration of 2,000 µg/l by extraction with C18 functionalized magnetic particles (DYNABEADS RPC18 from Invitrogen). According to the manufacturer's specification the stock suspension of these particles contained 12.5 mg/ml extraction material. A working suspension of the particles was prepared (by removing the original suspension matrix after magnetic immobilization, washing with trichloroacetic acid (0.1%), re-suspension in ethanol); this working solution contained 1.25 mg/ml extraction material. 10 µl aliquots of the plasma sample were extracted with different volumes of this working solution (sample 4-1 with 100 µl; sample 4-2 with 75 µl; sample 4-3 with 50 µl; sample 4-4 with 25 µl; sample 4-5 with 10 µl. The absolute amount of extraction material applied to 10 µl of sample was thus 125 µg, 94 µg, 62.5 µg, 31 µg, and 12.5 µg, respectively, for sample 4-1 to 4-5. For extraction the bead suspension was transferred in the described concentrations to polypropylene reaction tubes; the matrix (ethanol) was removed during magnetic immobilization of the particles. The magnet was removed from the samples; plasma was added, 100 µl of water were added, and the mixture was homogenized with a pipette. Subsequently the liquid matrix was removed during magnetic immobilization of the particles; particles were re-suspended and washed with 500 µl water; the fluid was removed during magnetic immobilization after one minute. For elution the particles were re-suspended in 100 µl of methanol/formic acid (0.1%) (9/1). The extract was recovered during magnetic immobilization of the particles. All extraction experiments were done in duplicate. All sample duplicates (1-4-5, A/B) were analyzed with LC-MS/MS in duplicate in one batch. Mean peak areas were calculated. The mean peak area of the pure solution was 205,176; the mean peak area of the plasma extract obtained by protein precipitation was 143,957; the mean peak area of the plasma extract obtained by solid phase extraction was 207,100. The mean peak areas of the samples 4-1 to 4-5 were as follows: 216,811; 143,596; 130,349; 116,332; 83,632. Thus the extraction efficacy of protein precipitation was 70%, that is to say, about 70% of the amount of analyte (itraconazol in this case) present in the sample was recovered by the extraction process; the extraction efficacy of solid phase extraction using 100 mg of extraction material (column material) was 100%; the extraction efficacy of magnetic particle extraction was about 100% using 125 µg of extraction material, 70% using 94 µg of extraction material, 64% using 62,5 µg extraction material, 57% using 31 µg extraction material, and 40% using 12,5 µg. This experiment shows the surprising effect that 12.5 µg C18-functionalized magnetic particles had about the same extraction efficacy as 1,000 µg of C18 functionalized extraction material used in a solid phase extraction protocol for the quantitative analysis of a representative small molecule analyte by LC-MS/MS. This corresponds to a mass ratio of 1/80.

EXAMPLE 12

Sample Preparation for Liquid Chromatography-tandem Mass Spectrometry

As a representative analyte, the antimycotic drug itraconazole was extracted from patients' samples by use of small quantities of C18-modified ferromagnetic micro particles. The extracts were submitted to LC-MS/MS analysis. Extraction recovery, linearity and reproducibility of the method were assessed. 125 µg of functionalized micro particles was sufficient to extract the target analyte from 10 µl of plasma with a recovery rate of approximately 100%. Applying this extraction protocol linearity (r>0.9) and reproducibility of quantitative results (inter-assay coefficients of variation ≦7%) was found. C18-functionalized ferromagnetic particles can be used to efficiently extract small molecules analytes from complex biological matrices for quantitative analyses using liquid chromatography-tandem mass spectrometry. Based on this observation the development of fully automated sample preparation modules for liquid chromatography-tandem mass spectrometry is an interesting option.

Plasma samples were extracted using C18-functionalized ferromagnetic micro-particles (Dynal DYNABEADS RPC18, Invitrogen, Karlsruhe, Germany; 12.5 mg/mL; mean particle diameter 1 µm). To prepare a working micro-particle suspension, 200 µl of the original particle suspension were transferred into a standard 2 ml polypropylene reaction tubes placed in a magnetic particle separator (Dynal MPC-S Magnetic Particle Concentrator, Product No. 120.20, Invitrogen. A permanent magnet was introduced into the separator device, leading to immobilization of the micro-particles upon the wall of the tube. The particle-free fluid was removed with a pipette tip; then, the magnet was removed from the separator device. For conditioning of the beads, 1 ml of 0.1% trichloric acid was dispensed into the tube; the particle pellet was re-dissolved by multiple pipetting. The magnet bar was introduced again and trichloric acid was removed. The conditioned beads were re-suspended in 2 ml of water, to obtain an amount of 1.25 µg of C18-functionalized extraction material in 1 µl of this magnetic particle working suspension.

For the preparation of plasma samples for the quantification of itraconazole by LC-MS/MS, 10 µl of an internal standard solution (compound R51012 (14); 1,000 µg/l in methanol/water (1/1)) were pipetted into a 1.5 ml reaction tube, and 10 µl of plasma were added. For mixing, the content of the tubes was aspirated and dispensed with the pipette tip several times. Then 100 µl of the magnetic particle working suspension was added; after mixing, analyte adsorption to the extraction material was allowed for two minutes. The sample matrix was then removed with a pipette tip after again inserting the magnet into the separator device. The magnet was removed, 500 µl of water was added for washing, and after immobilization of the particles the water was discarded. For analyte elution, 100 µl of acetonitrile/formic acid (0.1%) (90/10) was added, particles were re-suspended and finally immobilized to allow the transfer of the extract into HPLC vials. LC-MS/MS analysis of the extract was performed using a Waters Micromass Quattro Ultima Pt instrument, similar to a previously described (Vogeser M, et al. Clin Chem Lab Med 41 (2003) 915-920.), but without further clean-up.

To investigate the recovery rate of the extraction procedure and to characterize ion suppression properties of the entire analytical method, a plasma sample containing 2,000 µg/l itraconazole was extracted; the extract was analyzed by LC-MS/MS, and the peak area in the multiple reaction monitoring trace of itraconazole was recorded. For comparison, a pure solution of itraconazole in water/methanol was analyzed (200 µg/l, since the extraction protocol included dilution). The mean peak areas from four experiments differed less then 5% between pure solution and plasma extracts. Thus, 12.5 µg of extraction material was sufficient for full recovery extraction of 1 µl of plasma, avoiding ion suppression. Standard extraction protocols employing solid phase extraction cartridges usually extract 1 µl of sample with 1 mg of extraction material.

A basic validation protocol was performed in four independent analytical series. In each series a five-point calibration was performed (2,000, 1,000, 500, 250, 125 µg/l). Linear calibration functions (r>0.99) were observe in all series. In these series, aliquots of itraconazole containing plasma pools in three different concentration levels were analyzed in triplicate to calculate a total coefficient of variation (n=12). CVs between 5.4% and 7.0% were found for mean analyte concentrations ranging from 111 µg/l to 2,652 µg/l.

What is claimed is:

1. A method for extracting a compound from a sample comprising the steps of providing a liquid biological sample comprising the compound, the compound having a molecular weight between 50 and about 700 Da, contacting the sample with an amount of magnetic particles, the particles having a hydrophobic surface, incubating the sample and the particles whereby the compound is adsorbed onto the hydrophobic surface, separating the particles from the sample by applying a magnetic field, and eluting the compound from the particles, thereby extracting the compound from the sample.

2. The method of claim 1 wherein the compound has a molecular weight between 100 Da and about 500 Da.

3. The method of claim 1 wherein the sample is selected from the group consisting of serum, plasma, whole blood, and hemolyzed blood.

4. The method of claim 1 wherein the compound is selected from the group consisting of biologically active compounds and metabolites thereof.

5. The method of claim 1 wherein the compound is selected from the group consisting of folate, itraconazole, tacrolimus, everolimus, rapamycin, mycophenolate mofetil, mycophenolic acid, cyclosporine, azathioprine, methylprednisolone, amphetamine, cocaine, tetrahydrocannabinol, and phencyclidine.

6. A method for purifying a compound from a sample comprising the steps of providing liquid biological sample comprising the compound, the compound having a molecular weight between 50 and about 700 Da, contacting the sample with an amount of functionalized magnetic particles, the particles having a hydrophobic surface, incubating the sample and the particles whereby the compound is adsorbed onto the hydrophobic surface, separating the particles from the liquid sample by applying a magnetic field and removing the liquid sample, and eluting the compound from the particles, thereby purifying the compound.

7. The method of claim 6 wherein the surface of the magnetic particles is functionalized with a chemical group selected from the group consisting of a C4-C30 alkyl group, a copolymer of 1-vinyl-pyrrolidon and a comdivinylbenzene, and a copolymer of styrene and divinylbenzene.

8. A method for mass spectrometric analysis of a compound having a molecular weight between 50 and about 700 Da in a biological sample comprising the steps of providing a liquid biological sample comprising the compound, contacting the sample with an amount of magnetic particles, the particles having a hydrophobic surface, incubating the sample and the particles whereby the compound is adsorbed onto the hydrophobic surface, separating the particles from the liquid sample by applying a magnetic field and removing the liquid sample, eluting the compound from the particles, fractionating the eluate by way of liquid chromatography, and analyzing the compound in a fraction obtained from the chromatography step by way of mass spectrometry.

9. The method of claim 8 wherein the surface of the magnetic particles is functionalized with a chemical group selected from the group consisting of a C4-C30 alkyl group, a copolymer of 1-vinyl-pyrrolidon and a comdivinylbenzene, and a copolymer of styrene and divinylbenzene.

10. The method of claim 8 wherein the compound has a molecular weight between 100 and about 500 Da.

11. The method of claim 8 wherein the compound is selected from the group consisting of folate, itraconazole, tacrolimus, everolimus, rapamycin, mycophenolate mofetil, mycophenolic acid, cyclosporine, azathioprine, methylprednisolone, amphetamine, cocaine, tetrahydrocannabinol, and phencyclidine.

* * * * *